United States Patent
Volosin et al.

(10) Patent No.: US 11,633,614 B2
(45) Date of Patent: Apr. 25, 2023

(54) WEARABLE CARDIAC DEVICE TO MONITOR PHYSIOLOGICAL RESPONSE TO ACTIVITY

(71) Applicant: ZOLL Medical Corporation, Chelmsford, MA (US)

(72) Inventors: Kent Volosin, Mars, PA (US); Ramu Perumal, Gibsonia, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 93 days.

(21) Appl. No.: 16/417,688

(22) Filed: May 21, 2019

(65) Prior Publication Data

US 2019/0358464 A1 Nov. 28, 2019

Related U.S. Application Data

(60) Provisional application No. 62/676,304, filed on May 25, 2018.

(51) Int. Cl.
*A61B 5/00* (2006.01)
*A61N 1/39* (2006.01)
(Continued)

(52) U.S. Cl.
CPC .......... *A61N 1/3987* (2013.01); *A61B 5/0245* (2013.01); *A61B 5/1102* (2013.01);
(Continued)

(58) Field of Classification Search
None
See application file for complete search history.

(56) References Cited

U.S. PATENT DOCUMENTS 6,361,503 B1 * 3/2002 Starobin ............... A61B 5/349
600/508
7,974,689 B2 7/2011 Volpe et al.
(Continued)

OTHER PUBLICATIONS

Erne, Paul, Beyond auscultation—acoustic cardiography in the diagnosis and assessment of cardiac disease, Swiss Med Wkly 2008;138(31-32):439-452—www.smw.ch.
(Continued)

*Primary Examiner* — John R Downey
*Assistant Examiner* — Anant A Gupta
(74) *Attorney, Agent, or Firm* — The Webb Law Firm

(57) ABSTRACT

A patient-worn ambulatory cardiac monitoring device for monitoring a patient during a patient activity includes at least one physiological sensor configured to detect signals indicative of cardiac activity, an activity sensor and associated circuitry configured to monitor patient movements, and a vibrational sensor configured to monitor a cardio-vibrational signal of the patient. The at least one physiological sensor can include one of an ECG sensor and a heart rate sensor. At least one processor in communication with the at least one physiological sensor, the activity sensor, and the vibrational sensor, is configured to measure, during the patient activity, at least one time interval between an ECG fiducial point in an ECG signal and a cardio-vibrational fiducial point in the cardio-vibrational signal during a cardiac cycle of the patient's heart.

21 Claims, 20 Drawing Sheets

(51) Int. Cl.
  *A61B 5/0245* (2006.01)
  *A61B 5/11* (2006.01)
  *A61B 5/332* (2021.01)
  *A61B 5/352* (2021.01)
  *A61B 5/366* (2021.01)

(52) U.S. Cl.
  CPC ............ *A61B 5/1118* (2013.01); *A61B 5/332* (2021.01); *A61B 5/352* (2021.01); *A61B 5/366* (2021.01); *A61B 5/6805* (2013.01); *A61B 5/7275* (2013.01); *A61B 5/742* (2013.01); *A61N 1/3904* (2017.08)

(56) References Cited

U.S. PATENT DOCUMENTS

| | | | |
|---|---|---|---|
| 9,737,262 B2 | 8/2017 | Donnelly et al. | |
| 9,814,894 B2 | 11/2017 | Kaib et al. | |
| 2009/0299203 A1* | 12/2009 | De Voir | A61B 5/283 600/509 |
| 2010/0268059 A1* | 10/2010 | Ryu | A61B 5/283 600/407 |
| 2010/0298899 A1 | 11/2010 | Donnelly et al. | |
| 2011/0319778 A1* | 12/2011 | Sweeney | A61B 5/02133 607/18 |
| 2012/0165890 A1* | 6/2012 | Min | A61N 1/36585 607/23 |
| 2015/0005588 A1 | 1/2015 | Kaib | |
| 2015/0202494 A1* | 7/2015 | Hollenbach | A61B 5/1118 700/91 |
| 2016/0004831 A1 | 1/2016 | Carlson et al. | |
| 2016/0135706 A1* | 5/2016 | Sullivan | A61B 5/316 600/509 |
| 2016/0270738 A1* | 9/2016 | Volpe | A61B 5/25 |
| 2017/0100081 A1* | 4/2017 | Thakur | A61B 5/7275 |
| 2017/0188979 A1 | 7/2017 | Volpe | |
| 2017/0245808 A1* | 8/2017 | Jain | A61B 5/746 |
| 2017/0337033 A1* | 11/2017 | Duyan | G06F 3/165 |
| 2018/0001174 A1* | 1/2018 | Aoshima | A63B 69/0028 |
| 2018/0020931 A1 | 1/2018 | Shusterman | |
| 2019/0133516 A1* | 5/2019 | Banet | A61B 5/02055 |

OTHER PUBLICATIONS

Dillier, MD, Roger, et al., Assessment of Systolic and Diastolic Function in Asymptomatic Subjects using Ambulatory Monitoring with Acoustic Cardiography, Luzerner Kantonsspital, Lucerne, Switzerland.

Chao, Tze-Fan, et al. Electromechanical Activation Time in the Prediction of Discharge Outcomes in Patients Hospitalized with Acute Heart Failure Syndrome, Inter Med 49: 2031-2037, 2010.

Sung, Shih-Hsien, et al., Use of Acoustic Cardiography To Guide Outpatient Therapy of Patients With Acute Heart Failure Syndrome, ACC.14, JACC Apr. 2014, vol. 63, Issue 12, http://content.onlinejacc.org/.

PCT International Search Report and Written Opinion for PCT Application No. PCT/US2019/033199, dated Oct. 17, 2019, 20 pages.

* cited by examiner

| Date | EMAT (ms) | HR (average per session) |
|---|---|---|
| Activity 1 | 90 | 130 |
| Activity 2 | 98 | 136 |
| Activity 3 | 102 | 133 |
| Activity 4 | 106 | 132 |
| Activity 5 | 105 | 133 |
| Activity 6 | 106 | 131 |
| Activity 7 | 111 | 135 |

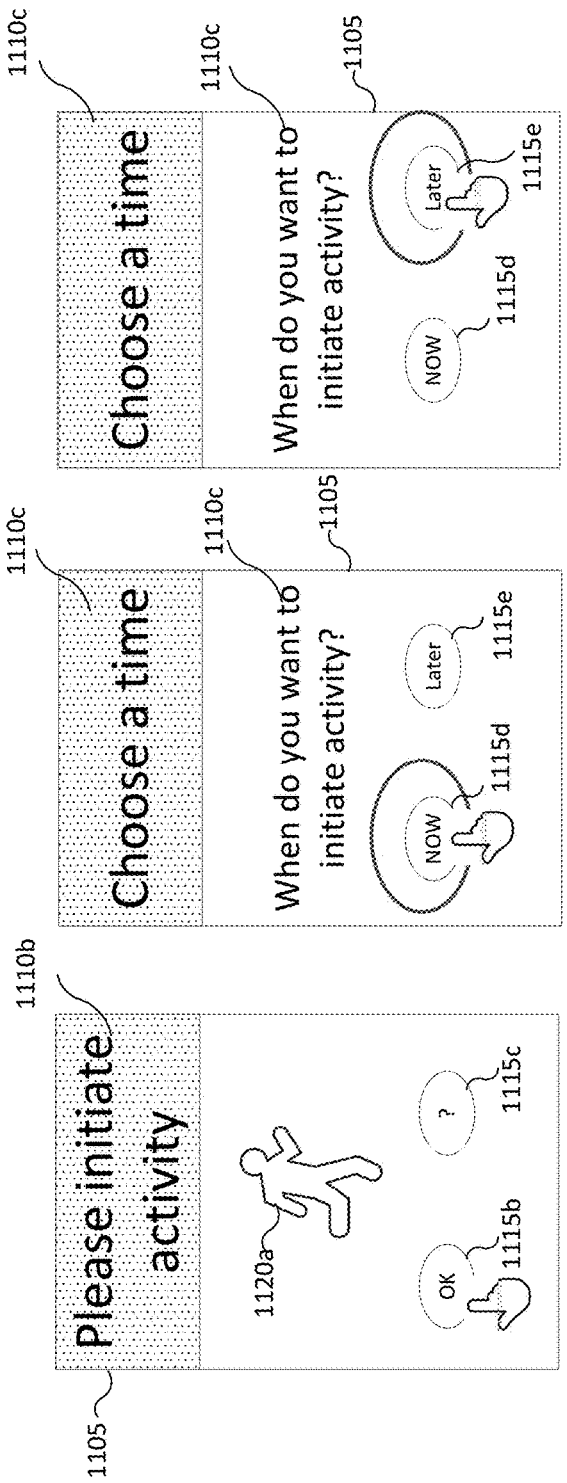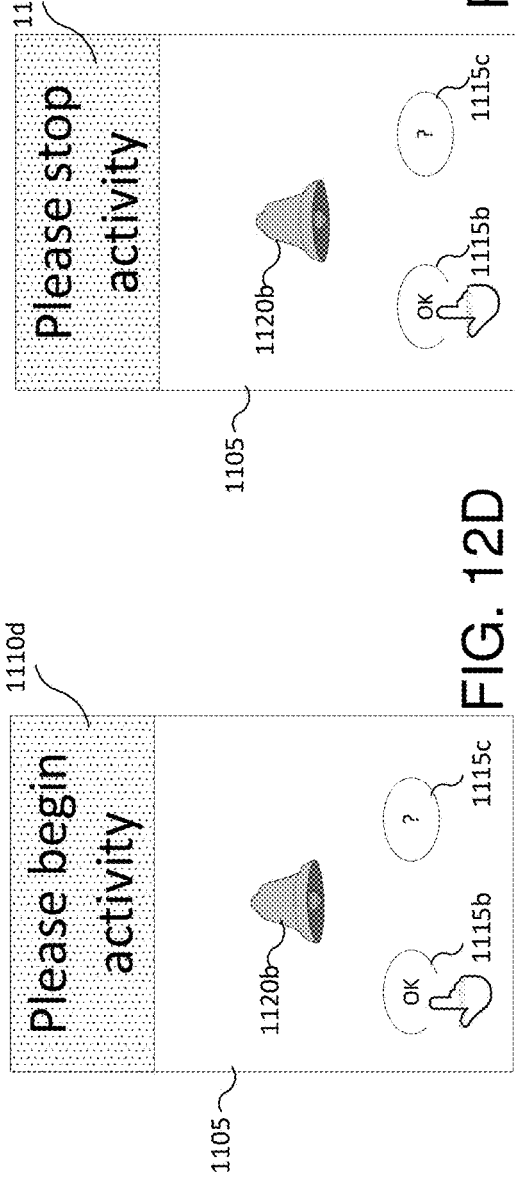

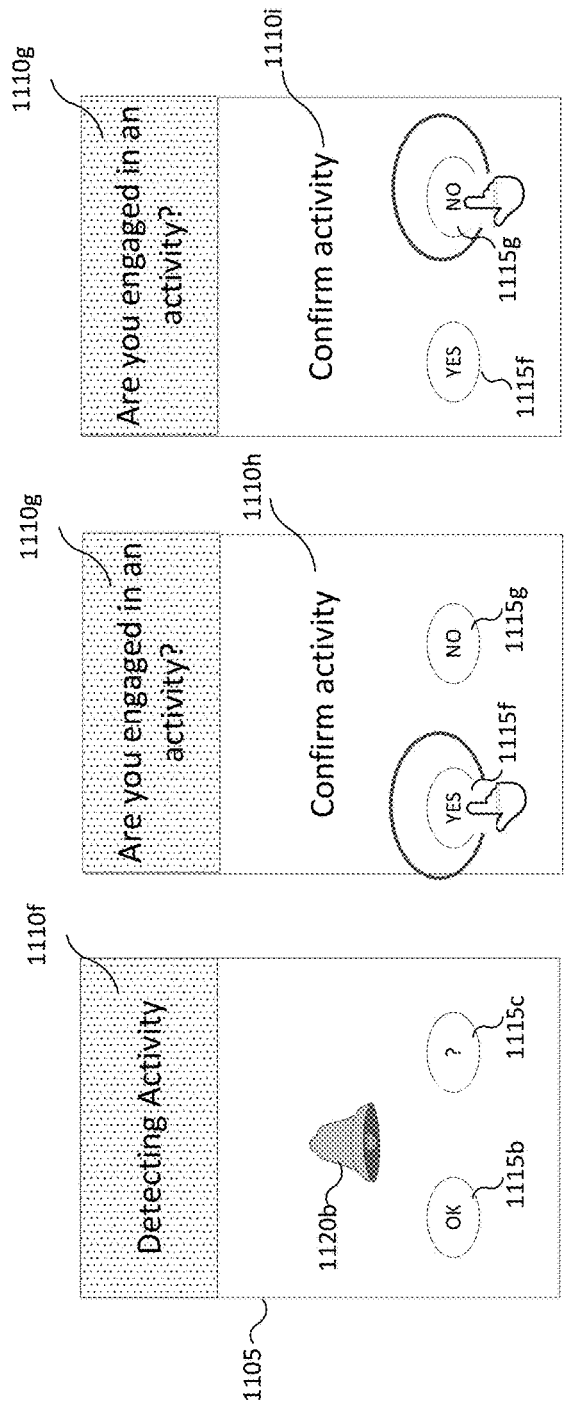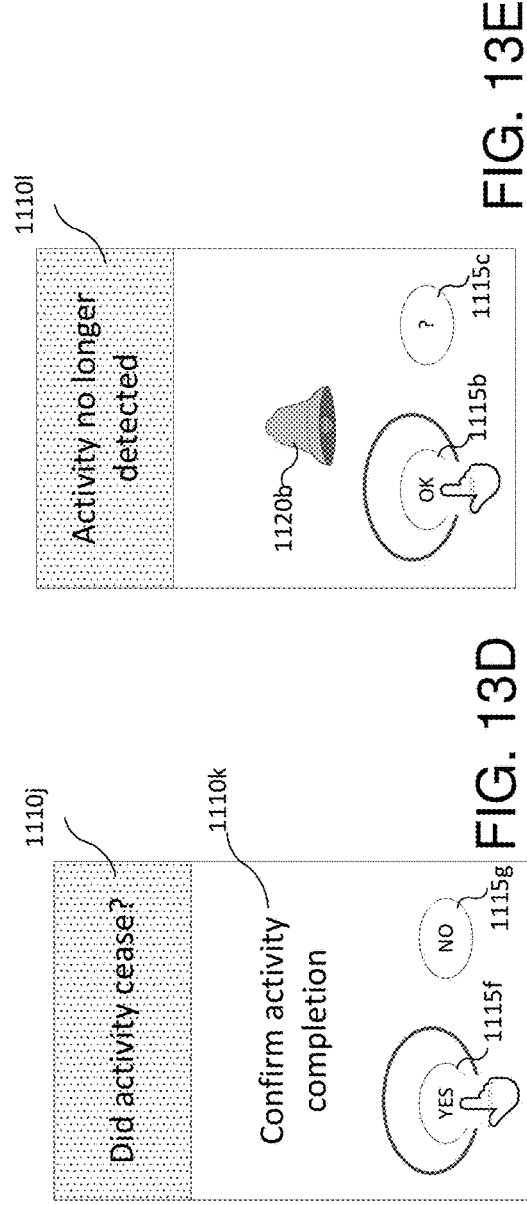
FIG. 13A  FIG. 13B  FIG. 13C  FIG. 13D  FIG. 13E

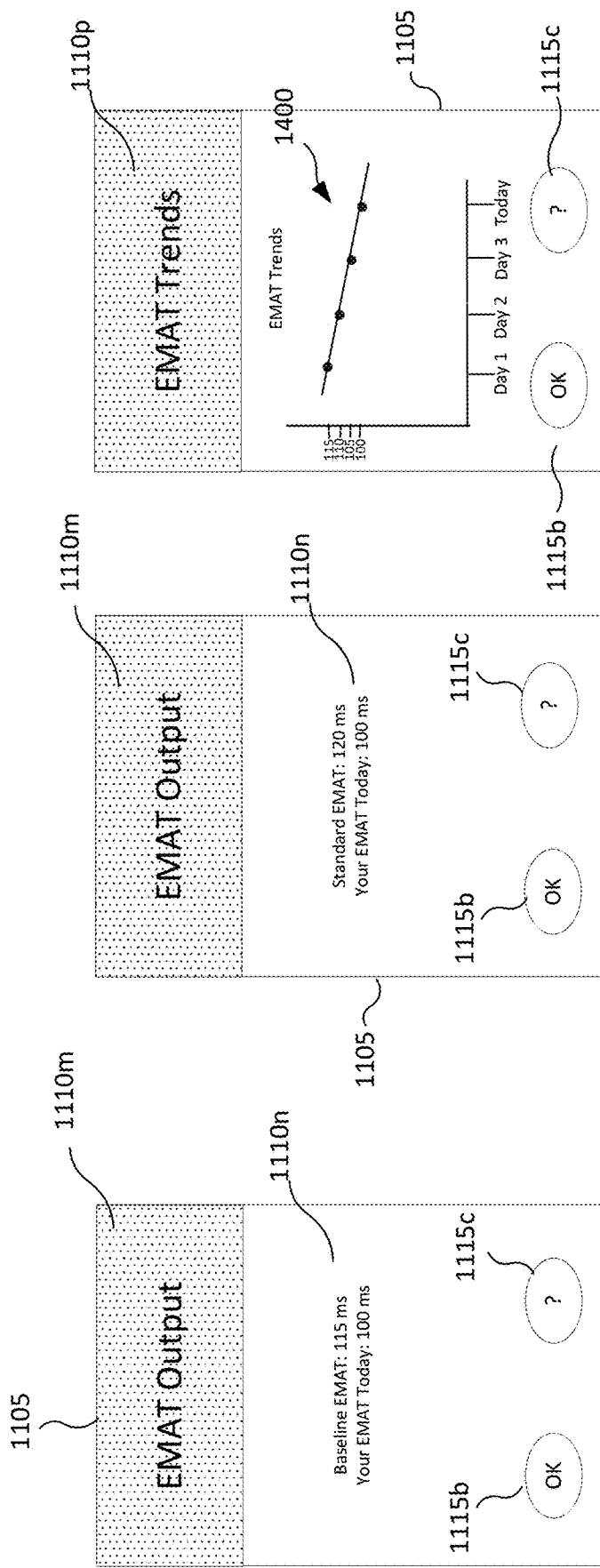

WEARABLE CARDIAC DEVICE TO MONITOR PHYSIOLOGICAL RESPONSE TO ACTIVITY

CROSS-REFERENCE TO RELATED APPLICATIONS

This application claims priority under 35 U.S.C. § 119(e) to U.S. Provisional Patent Application Ser. No. 62/676,304 filed May 25, 2018, titled "Wearable Cardiac Device To Monitor Physiological Response To Activity," the entirety of which is hereby incorporated by reference.

BACKGROUND

The present disclosure is directed to wearable cardiac devices, systems, and methods for monitoring physiological status of patients during periods of patient activity.

A patient suffering from heart failure experiences symptoms caused by a weak or damaged heart contracting inefficiently and failing to pump effectively to circulate oxygenated blood through the body. A heart may be weakened by, for example, abnormal heart rhythms (e.g., heart arrhythmias), high blood pressure, coronary artery disease, myocardial infarction, and myocarditis.

Left untreated, heart failure could lead certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia.

Cardiac arrest can occur when various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for supporting life. It is generally useful to monitor heart failure patients in order to assess heart failure symptoms early and provide interventional therapies as soon as possible.

SUMMARY

In one example, a patient-worn ambulatory cardiac monitoring device for monitoring a patient during a patient activity includes at least one physiological sensor configured to detect signals indicative of cardiac activity including one of an ECG sensor and a heart rate sensor. The device also includes an activity sensor and associated circuitry configured to monitor patient movements, a vibrational sensor configured to monitor a cardio-vibrational signal of the patient; and at least one processor in communication with the at least one physiological sensor, the activity sensor, and the vibrational sensor. In examples, the processor is configured to measure, during the patient activity, at least one time interval between an ECG fiducial point in an ECG signal and a cardio-vibrational fiducial point in the cardio-vibrational signal during a cardiac cycle of the patient's heart.

Implementations of the device may include one or more of the following features.

In examples, the at least one physiological sensor is configured to be in contact with a torso of the patient and monitor an ECG signal of the patient.

In examples, the activity sensor includes an accelerometer.

In examples of the device, the at least one processor is configured to record a baseline time interval for the at least one time interval during a baseline period, and is configured to compare the at least one time interval with the baseline time interval, and provide an output based on the comparison. In some examples, the at least one processor is configured to provide the output based on the comparison when the at least one time interval falls outside of a range of within at least one of: 1% of the baseline time interval, 2% of the baseline time interval, 5% of the baseline time interval, 10% of the baseline time interval, 15% of the baseline time interval, and 20% of the baseline time interval. The at least one processor can be configured to identify an improving or worsening heart failure condition of the patient based on the output.

In examples, the device further includes a network interface configured to transmit the output to a remote server.

The at least one processor can be configured to retrieve at least one of a standard time interval and a standard time interval range. In examples, the at least one processor is configured to compare the at least one time interval with the retrieved at least one of the standard time interval and the standard time interval range, and provide an output based on the comparison. In some examples, the standard time interval includes a value selected from a range of about 80 ms to about 150 ms. In some examples, the standard time interval includes a value selected from a range of about 100 ms to about 140 ms. In some examples, the standard time interval includes a value selected from a range of about 110 ms to about 130 ms. In some examples, the standard time interval includes at least one of 80 ms, 90 ms, 100 ms, 105 ms, 110 ms, 115 ms, 120 ms, 125 ms, 130 ms, 135 ms, 140 ms, 145 ms and 150 ms.

In examples, the standard time interval range comprises a range of about 80 ms to about 150 ms. In some examples, the standard time interval range can comprise a range of about 100 ms to about 140 ms. In some examples, the standard time interval range can comprise a range of about 110 ms to about 130 ms. In examples, the standard time interval range can comprise a range that spans at least one of at least 10 ms, at least 15 ms, at least 20 ms, at least 30 ms, at least 40 ms, at least 50 ms, at least 60 ms and at least 70 ms within the range of about 80 ms to about 150 ms. In examples, the standard time interval range includes at least one of 80 ms-85 ms, 85 ms-90 ms, 90 ms-95 ms, 95 ms-100 ms, 100 ms-105 ms, 105 ms-110 ms, 110 ms-115 ms, and 115 ms-120 ms, 120 ms-125 ms, 125 ms-130 ms, 130 ms-135 ms, 135 ms-140 ms, 140 ms-145 ms, and 145 ms-150 ms. In examples, the at least one processor can be configured to provide the output based on the comparison when the at least one time interval falls outside of a range of within at least one of: 1% of the standard time interval, 2% of the standard time interval, 5% of the standard time interval, 10% of the standard time interval, 15% of the standard time interval, and 20% of the standard time interval. The at least one processor can configured to identify an improving or worsening heart failure condition of the patient based on the output. In examples, the device further includes a network interface configured to transmit the output to a remote server.

In examples, the at least one processor is configured to compare the at least one time interval with a subsequent time interval representing a subsequently monitored cardiac cycle during a subsequent patient activity, provide an output based on the comparison, and determine an improving or worsening heart failure condition of the patient based on the output. In some examples, the device further includes a network interface configured to transmit the output to a remote server.

In examples, the at least one time interval includes a plurality of time intervals measured during a plurality of patient activities. The at least one processor can be configured to monitor for one or more trends in the plurality of time intervals, and provide an output based on the one or more trends. The device can further include a network interface configured to transmit the output to a remote server. In examples, the at least one processor is further configured to determine an improving or worsening heart failure condition of the patient based on the output.

In examples, the at least one time interval is indicative of systolic function of the patient's heart.

In examples, the at least one processor is further configured to determine that the patient is engaged in the patient activity based on detecting a predetermined elevation in a heart rate derived from an ECG signal of the patient, and store a activity start marker in a memory of the device on determining that the patient is engaged in the patient activity. In some examples, the predetermined elevation of the heart rate is an elevation of at least between 5-20% of a baseline or standard heart rate of the patient. In some examples, the predetermined elevation of the heart rate is over a duration of at least between 1 to 5 minutes. In examples, the at least one processor is configured to prompt the patient to confirm that the patient is engaged in the patient activity prior to storing the activity start marker in the memory. The at least one processor can be configured to determine that the patient is engaged in the patient activity further based on signals from the activity sensor indicating patient movements.

In examples, the at least one processor is further configured to measure, during the patient activity, a cardio-vibrational time interval measured from a first cardio-vibrational fiducial point of an S1 cardio-vibrational biomarker to a second cardio-vibrational fiducial point of an S2 cardio-vibrational biomarker for the cardiac cycle. In some examples, the cardio-vibrational time interval includes a left ventricular systolic time (LVST) interval.

In examples, the at least one processor is further configured to measure, during the patient activity, a S3 cardio-vibrational biomarker strength derived from the cardio-vibrational signal.

In examples, the device includes a wearable defibrillator. In some examples, the device further includes a garment configured to be worn about the torso of the patient, and at least two therapy electrodes supported by the garment and configured to deliver energy to the torso of the patient. In examples, the at least one physiological sensor is supported by the garment. The device can be configured to be worn for a prescribed period of wear of at least between one week and two weeks, two weeks and one month, one month and two months, two months and three months, and three months and six months.

In some examples of the device, the vibrational sensor includes the activity sensor.

In examples, the patient activity has an activity duration of between at least 3 to 6 minutes, between at least 6 to 12 minutes, between at least 12 to 15 minutes, between at least 15 to 20 minutes, between at least 20 to 30 minutes, between at least 30 to 45 minutes, and between at least 45 minutes to an hour.

In some examples, the device is configured to prompt the patient to engage in the patient activity. The patient activity can be a prescribed activity prompted at scheduled intervals. In examples, a network interface is configured to communicate with a remote server, and the remote server is configured to transmit an instruction to the device via the network interface to prompt the patient to initiate the patient activity.

In examples, the device further includes a user interface configured to guide the patient through the patient activity.

In examples, the at least one time interval begins from the ECG fiducial point on a P-wave segment of the ECG signal and ends at the cardio-vibrational fiducial point within an S1 cardio-vibrational biomarker of the cardio-vibrational signal.

In examples, the at least one time interval begins from the ECG fiducial point on a P-Q segment of the ECG signal and ends at the cardio-vibrational fiducial point within an S1 cardio-vibrational biomarker of the cardio-vibrational signal.

In examples, the at least one time interval begins from the ECG fiducial point on a Q-wave segment of the ECG signal and ends at the cardio-vibrational fiducial point within an S1 cardio-vibrational biomarker of the cardio-vibrational signal.

In examples, the at least one time interval begins from the ECG fiducial point is on an R-wave segment of the ECG signal and ends at the cardio-vibrational fiducial point within an S1 cardio-vibrational biomarker of the cardio-vibrational signal. In some examples, the at least one time interval begins from the ECG fiducial point at the beginning of the R-wave segment of the ECG signal and ends at the cardio-vibrational fiducial point within the S1 cardio-vibrational biomarker of the cardio-vibrational signal.

In examples, the at least one processor can be configured to measure an RR interval of the ECG signal and calculate a ratio of the at least one time interval to the RR interval.

In examples, the at least one time interval begins from the cardio-vibrational fiducial point within an S2 cardio-vibrational biomarker of the cardio-vibrational signal and the ECG fiducial point at an onset of a next Q wave in the ECG signal.

In examples, the at least one time interval includes an LDPT interval.

In examples, the at least one time interval includes an electromechanical activation time (EMAT) interval. In some examples, the at least one processor can be configured to calculate a ratio of at least one of a: EMAT/LVST, EMAT/LDPT, and EMAT/RR.

In one example, a patient-worn ambulatory cardiac monitoring device for monitoring a patient during a patient activity includes at least one ECG sensor in contact with a torso of the patient and configured to monitor an ECG signal of the patient, an accelerometer and associated circuitry configured to monitor patient movements, a vibrational sensor configured to monitor a cardio-vibrational signal of the patient, and at least one processor in communication with the at least one ECG sensor, the accelerometer, and the vibrational sensor. The at least one processor can be configured to measure, during the patient activity, at least one of: a cardio-vibrational strength of an cardio-vibrational biomarker, and a cardio-vibrational interval from a first cardio-vibrational fiducial point to a second cardio-vibrational fiducial point in the cardio-vibrational signal during a cardiac cycle of the patient's heart.

Implementations of the device may include one or more of the following features.

In examples, the cardio-vibrational strength includes an S3 cardio-vibrational biomarker strength.

In examples, the first cardio-vibrational fiducial point is within a first cardio-vibrational biomarker of the cardio-vibrational signal and the second cardio-vibrational fiducial point is within a second cardio-vibrational biomarker of the cardio-vibrational signal.

In examples, the first cardio-vibrational fiducial point is within an S1 cardio-vibrational biomarker of the cardio-vibrational signal and the second cardio-vibrational fiducial point is within an S2 cardio-vibrational biomarker of the cardio-vibrational signal.

In examples, the at least one processor is further configured to measure, during the patient activity, at least one time interval from an ECG fiducial point to a cardio-vibrational fiducial point during the cardiac cycle of the patient's heart. In some examples, the ECG fiducial point is a fiducial point on a P-wave segment of the ECG signal and the cardio-vibrational fiducial point is within an S1 cardio-vibrational biomarker of the cardio-vibrational signal. In some examples, the ECG fiducial point is a fiducial point on a P-Q segment of the ECG signal and the cardio-vibrational fiducial point is within an S1 cardio-vibrational biomarker of the cardio-vibrational signal. In some examples, the ECG fiducial point is a fiducial point on a Q-wave segment of the ECG signal and the cardio-vibrational fiducial point is within an S1 cardio-vibrational biomarker of the cardio-vibrational signal. In some examples, the ECG fiducial point is a fiducial point on an R-wave segment of the ECG signal and the cardio-vibrational fiducial point is within an S1 cardio-vibrational biomarker of the cardio-vibrational signal. The ECG fiducial point can be at the beginning of the R-wave segment of the ECG signal and the cardio-vibrational fiducial point is within the S1 cardio-vibrational biomarker of the cardio-vibrational signal. In some examples, the at least one processor is configured to measure an RR interval of the ECG signal and calculate a ratio of the at least one time interval to the RR interval. In examples, the at least one time interval includes an electromechanical activation time (EMAT) interval.

In examples, the at least one processor is configured to record a baseline cardio-vibrational strength during a baseline period. The at least one processor can be configured to compare the cardio-vibrational strength with the baseline cardio-vibrational strength, and provide an output based on the comparison. In some examples, the at least one processor is configured to provide the output based on the comparison when the cardio-vibrational strength falls outside of a range of within at least one of: 1% of the baseline cardio-vibrational strength, 2% of the baseline cardio-vibrational strength, 5% of the baseline cardio-vibrational strength, 10% of the baseline cardio-vibrational strength, 15% of the baseline cardio-vibrational strength, and 20% of the baseline cardio-vibrational strength. The at least one processor can be configured to identify an improving or worsening heart failure condition of the patient based on the output. In examples, the device further includes a network interface configured to transmit the output to a remote server.

In examples, the at least one processor is configured to retrieve at least one of a standard cardio-vibrational strength and a standard cardio-vibrational strength range. The at least one processor can be configured to compare the cardio-vibrational strength with the retrieved at least one of the standard cardio-vibrational strength and the standard cardio-vibrational strength range, and provide an output based on the comparison.

In examples, the standard cardio-vibrational strength includes a value selected from a range of 3 to 7 strength units. In examples, the standard cardio-vibrational strength includes a value selected from a range of 4 to 6 strength units. In examples, the standard cardio-vibrational strength includes a value of at least one of: 3 strength units, 4 strength units, 5 strength units, and 6 strength units.

In examples, the standard cardio-vibrational strength range includes a range from of 3 to 7 strength units. In examples, the standard cardio-vibrational strength range includes a range of 4 to 6 strength units. In examples, the standard cardio-vibrational strength range includes at least one of 3 to 4 strength units, 4 to 5 strength units, and 5 to 6 strength units. The at least one processor can be configured to provide the output based on the comparison where the cardio-vibrational strength falls outside of a cardio-vibrational strength range of within at least one of: 1% of the standard cardio-vibrational strength, 2% of the standard cardio-vibrational strength, 5% of the standard cardio-vibrational strength, 10% of the standard cardio-vibrational strength, 15% of the standard cardio-vibrational strength, and 20% of the standard cardio-vibrational strength. The at least one processor can be configured to identify an improving or worsening heart failure condition of the patient based on the output. In examples, the device further includes a network interface configured to transmit the output to a remote server.

In examples, the at least one processor can be configured to record a baseline cardio-vibrational interval during a baseline period. The at least one processor can be configured to compare the cardio-vibrational interval with the baseline cardio-vibrational interval, and provide an output based on the comparison. The at least one processor can be configured to provide an output based on the comparison when the cardio-vibrational interval falls outside of a range of within at least one of: 1% of the baseline cardio-vibrational interval, 2% of the baseline cardio-vibrational interval, 5% of the baseline cardio-vibrational interval, 10% of the baseline cardio-vibrational interval, 15% of the baseline cardio-vibrational interval, and 20% of the baseline cardio-vibrational interval. The at least one processor can be configured to identify an improving or worsening heart failure condition of the patient based on the output. In examples the device further includes a network interface configured to transmit the output to a remote server.

In examples, the at least one processor is configured to retrieve at least one of a standard cardio-vibrational interval and a standard cardio-vibrational interval range. The at least one processor can be configured to compare the cardio-vibrational interval with the retrieved at least one of the standard cardio-vibrational interval and the standard cardio-vibrational interval range, and provide an output based on the comparison. In examples, the at least one processor can be configured to provide the output based on the comparison when the cardio-vibrational interval falls outside of a range of within at least one of: 1% of the standard cardio-vibrational interval, 2% of the standard cardio-vibrational interval, 5% of the standard cardio-vibrational interval, 10% of the standard cardio-vibrational interval, 15% of the standard cardio-vibrational interval, and 20% of the standard cardio-vibrational interval. The at least one processor can be configured to identify an improving or worsening heart failure condition of the patient based on the output. In examples, the device further includes a network interface configured to transmit the output to a remote server.

In examples, the at least one processor is configured to compare the cardio-vibrational strength with a subsequent cardio-vibrational strength including a subsequently monitored cardiac cycle during a subsequent patient activity, determine an improving or worsening heart failure condition of the patient based on the comparison, and provide an output based on the comparison. The device can further include a network interface configured to transmit the output to a remote server.

In examples, the at least one processor is configured to compare the cardio-vibrational interval with a subsequent time interval during a subsequent patient activity, determine an improving or worsening heart failure condition of the patient based on the comparison, and provide an output based on the comparison. The device can further include a network interface configured to transmit the output to a remote server.

In examples, the at least one processor is further configured to measure a plurality of cardio-vibrational strengths measured during a plurality of patient activities. The at least one processor can be configured to monitor for one or more trends in the plurality of cardio-vibrational strengths, and provide an output based on the one or more trends in the plurality of cardio-vibrational strengths. In examples, the device further includes a network interface configured to transmit the output to a remote server. The at least one processor can be further configured to determine an improving or worsening heart failure condition of the patient based on the output.

In examples, the at least one processor is further configured to measure a plurality of cardio-vibrational intervals measured during a plurality of patient activities. The at least one processor can be configured to monitor for one or more trends in the plurality of cardio-vibrational intervals, and provide an output based on the one or more trends in the plurality of cardio-vibrational intervals. The device can further include a network interface configured to transmit the output to a remote server, and the at least one processor can be further configured to determine an improving or worsening heart failure condition of the patient based on the output.

In examples, the device includes a wearable defibrillator. In some examples, the device further includes a garment configured to be worn about the torso of the patient and at least two therapy electrodes supported by the garment and configured to deliver energy to the torso of the patient. In examples, the at least one ECG sensor is supported by the garment.

In examples, the patient activity includes a predetermined activity duration of between at least 3 to 6 minutes, between at least 6 to 12 minutes, between at least 12 to 15 minutes, between at least 15 to 20 minutes, between at least 20 to 30 minutes, between at least 30 to 45 minutes, between at least 45 minutes to an hour.

In examples, the device is configured to prompt the patient to engage in the patient activity. In some examples the patient activity is a prescribed activity prompted at scheduled intervals. In examples, the device further includes a network interface configured to communicate with a remote server, and the remote server is configured to transmit an instruction to the device via the network interface to prompt the patient to initiate the patient activity. In examples, the device further includes a user interface configured to guide the patient through the patient activity.

In examples, the at least one processor is further configured to determine that the patient is engaged in the patient activity based on detecting a predetermined elevation in a heart rate derived from the ECG signal of the patient, and store a activity start marker in a memory of the device on determining that the patient is engaged in the patient activity. In some examples, the predetermined elevation of the heart rate is elevated for at least between 5-20% of a baseline or standard heart rate of the patient. In examples, the predetermined elevation of the heart rate is over a duration of at least between 1 to 5 minutes. The at least one processor can be configured to prompt the patient to confirm that the patient is engaged in the patient activity prior to storing the activity start marker in the memory. The at least one processor can be configured to determine that the patient is engaged in the patient activity further based on signals from the accelerometer indicating patient movements.

In examples, the device is configured to be worn for a prescribed period of wear of at least between one week and two weeks, two weeks and one month, one month and two months, two months and three months, and three months and six months.

In examples of the device, the vibrational sensor includes the accelerometer.

In one example, a patient-worn ambulatory cardiac monitoring device for monitoring a patient during a patient activity includes at least one ECG sensor in contact with a torso of the patient and configured to monitor an ECG signal of the patient, an accelerometer and associated circuitry configured to monitor patient movements during the patient activity, a vibrational sensor configured to monitor a cardio-vibrational signal of the patient, and at least one processor in communication with the at least one ECG sensor, the accelerometer, and the vibrational sensor. The at least one processor is configured to derive, during the patient activity, at least one electromechanical time interval from an ECG fiducial point to a cardio-vibrational fiducial point during a cardiac cycle of the patient's heart during a systolic phase of the cardiac cycle of the patient's heart. The at least one processor is configured to monitor for one or more trends in the at least one electromechanical time interval indicating an improving or worsening heart failure condition of the patient, and provide an output based on the one or more trends.

Implementations of the device may include one or more of the following features.

In one example, a cardiac monitoring system for monitoring a patient during a patient activity, includes a patient-worn ambulatory cardiac monitoring device including a network interface, and a remote server in communication with the network interface of the patient-worn ambulatory cardiac monitoring device. The patient-worn ambulatory cardiac monitoring device can include a plurality of ECG sensors in contact with a torso of the patient and configured to monitor an ECG signal of the patient, an accelerometer configured to monitor patient movements during the patient activity, a vibrational sensor configured to monitor a cardio-vibrational signal of the patient, and at least one processor in communication with the plurality of ECG sensors, the accelerometer, and the vibrational sensor. The at least one processor can be configured to measure, during the patient activity, at least one of: an electromechanical time interval during a cardiac cycle between an ECG fiducial point on the ECG signal and a cardio-vibrational fiducial point in the cardio-vibrational signal, a cardio-vibrational strength of an cardio-vibrational biomarker, and a cardio-vibrational interval from a first cardio-vibrational fiducial point to a second cardio-vibrational fiducial point in the cardio-vibrational signal during the cardiac cycle of the patient's heart. The remote server can be configured to receive at least one of the electromechanical time interval, the cardio-vibrational strength, and the cardio-vibrational interval, and provide an output based on the at least one of the electromechanical time interval, the cardio-vibrational strength, and the cardio-vibrational interval. The at least one of the electromechanical time interval, the cardio-vibrational strength, and the cardio-vibrational interval is indicative of an improving or worsening heart failure condition of the patient.

Implementations of the system may include one or more of the following features.

In examples, the remote server is configured to generate a report to a caregiver of the patient, and the output is provided within the report to the caregiver of the patient.

In one example, a method of evaluating systolic function of a patient's heart during patient activity includes receiving an ECG signal from a plurality of ECG sensors in contact with a torso of a patient, receiving information relating to patient movements from an accelerometer disposed on the patient, receiving a cardio-vibrational signal of the patient from a vibrational sensor disposed on the patient, measuring at least one time interval between an ECG fiducial point on the ECG signal and a cardio-vibrational fiducial point in the cardio-vibrational signal of the patient during a systolic phase of a cardiac cycle of the patient's heart, and providing an output based on the at least one time interval, wherein the at least one time interval is indicative of an improving or worsening heart failure condition of the patient.

Implementations of the method may include one or more of the following features.

The method further can include determining an improving or worsening heart failure condition of the patient based on the output, and transmitting the output to a remote server via a network interface.

In examples, the method further includes recording a baseline time interval for the at least one time interval during a baseline period. The method can further include comparing the at least one time interval with the baseline time interval, and providing the output based on the comparison. In examples, providing the output occurs when the at least one time interval falls outside of a range of within at least one of: 1% of the baseline time interval, 2% of the baseline time interval, 5% of the baseline time interval, 10% of the baseline time interval, 15% of the baseline time interval, and 20% of the baseline time interval.

In examples, the method further includes retrieving at least one of a standard time interval and a standard time interval range, and comparing the at least one time interval with the retrieved at least one of the standard time interval and the standard time interval range, and providing the output based on the comparison. In some examples, the standard time interval includes a value selected from a range of about 80 ms to about 150 ms. The standard time interval can include a value selected from a range of about 100 ms to about 140 ms. The standard time interval can include a value selected from a range of about 110 ms to about 130 ms. In examples, the standard time interval includes at least one of 80 ms, 90 ms, 100 ms, 105 ms, 110 ms, 115 ms, 120 ms, 125 ms, 130 ms 135, 140 ms, 145, and 150 ms.

In examples, the standard time interval range comprises a range of about 80 ms to about 150 ms. The standard time interval range can comprise a range of about 100 ms to about 140 ms. The standard time interval range can comprise a range of about 110 ms to about 130 ms. In examples, the standard time interval range comprises a range that spans at least one of at least 10 ms, at least 15 ms, at least 20 ms, at least 30 ms, at least 40 ms, at least 50 ms, at least 60 ms and at least 70 ms within the values of about 80 ms to about 150 ms. In examples, the standard time interval range includes at least one of 80 ms-85 ms, 85 ms-90 ms, 90 ms-95 ms, 95 ms-100 ms, 100 ms-105 ms, 105 ms-110 ms, 110 ms-115 ms, and 115 ms-120 ms, 120 ms-125 ms, 125 ms-130 ms, 130 ms-135 ms, and 135 ms-140 ms.

In examples, the output is provided based on the comparison when the at least one time interval falls outside of a range of within at least one of: 1% of the standard time interval, 2% of the standard time interval, 5% of the standard time interval, 10% of the standard time interval, 15% of the standard time interval, and 20% of the standard time interval.

In examples, the method further includes comparing the at least one time interval with a subsequent time interval representing a subsequently monitored cardiac cycle during a subsequent patient activity, providing the output based on the comparison, and determining an improving or worsening heart failure condition of the patient based on the output. The method can further include transmitting the output to a remote server via a network interface.

In examples, the at least one time interval includes a plurality of time intervals measured during a plurality of patient activities, and the method further includes monitoring for one or more trends in the plurality of time intervals, and providing the output based on the one or more trends. The method can further include transmitting the output to a remote server via a network interface, and determining an improving or worsening heart failure condition of the patient based on the output.

In examples, the method further includes measuring, during the patient activity, a cardio-vibrational time interval measured from a first cardio-vibrational fiducial point of an S1 cardio-vibrational biomarker to a second cardio-vibrational fiducial point of an S2 cardio-vibrational biomarker for the cardiac cycle. In examples, the cardio-vibrational time interval includes a left ventricular systolic time (LVST) interval.

In examples, the method further includes measuring, during the patient activity, a S3 cardio-vibrational biomarker strength derived from the cardio-vibrational signal.

In examples, the at least one time interval begins from the cardio-vibrational fiducial point within an S2 cardio-vibrational biomarker of the cardio-vibrational signal and the ECG fiducial point at an onset of a next Q wave in the ECG signal. In some examples, the at least one time interval includes an LDPT.

In examples, the at least one time interval begins from the ECG fiducial point at the beginning of an R-wave segment and ends at the cardio-vibrational fiducial point within an S1 cardio-vibrational biomarker of the cardio-vibrational signal.

In examples, the at least one time interval includes an electromechanical activation time (EMAT) interval. The method can further include calculating at least one of a ratio of: EMAT/LVST, EMAT/LDPT, and EMAT/RR.

In one example, a patient-worn ambulatory cardiac monitoring device for monitoring a patient during a patient activity includes at least one physiological sensor configured to detect signals indicative of cardiac activity including one of an ECG sensor configured to monitor an ECG signal of the patient and a heart rate sensor. The device also includes an activity sensor and associated circuitry configured to monitor patient movements, a vibrational sensor configured to monitor a cardio-vibrational signal of the patient; and at least one processor in communication with the at least one physiological sensor, the activity sensor, and the vibrational sensor. In examples, the processor is configured to determine initiation of the patient activity, and measure, during the patient activity, at least one electromechanical time interval between an ECG fiducial point in an ECG signal and a cardio-vibrational fiducial point in the cardio-vibrational signal during a cardiac cycle of the patient's heart.

Implementations of the device may include one or more of the following features.

In examples, the at least one physiological sensor is configured to be in contact with a torso of the patient and monitor an ECG signal of the patient.

In examples, the activity sensor includes an accelerometer.

In examples of the device, the at least one processor is configured to record a baseline electromechanical time interval for the at least one electromechanical time interval during a baseline period, compare the at least one electromechanical time interval with the baseline electromechanical time interval, provide an output based on the comparison, and identify an improving or worsening heart failure condition of the patient based on the output. In some examples, the at least one processor is configured to provide the output based on the comparison when the at least one electromechanical time interval falls outside of a range of within at least one of: 1% of the baseline electromechanical time interval, 2% of the baseline electromechanical time interval, 5% of the baseline electromechanical time interval, 10% of the baseline electromechanical time interval, 15% of the baseline electromechanical time interval, and 20% of the baseline electromechanical time interval. The at least one processor can be configured to identify an improving or worsening heart failure condition of the patient based on the output.

In examples, the device further includes a network interface configured to transmit the output to a remote server.

The at least one processor can be configured to retrieve at least one of a standard electromechanical time interval and a standard electromechanical time interval range. In examples, the at least one processor is configured to compare the at least one electromechanical time interval with the retrieved at least one of the standard electromechanical time interval and the standard electromechanical time interval range, and provide an output based on the comparison. In some examples, the standard electromechanical time interval includes a value selected from a range of about 80 ms to about 150 ms, and the standard electromechanical time interval range includes a range of about 80 ms to about 150 ms. In some examples, the standard electromechanical time interval includes a value selected from a range of about 100 ms to about 140 ms. In some examples, the standard electromechanical time interval includes a value selected from a range of about 110 ms to about 130 ms. In some examples, the standard electromechanical time interval includes at least one of 80 ms, 90 ms, 100 ms, 105 ms, 110 ms, 115 ms, 120 ms, 125 ms, 130 ms, 135 ms, 140 ms, 145 ms and 150 ms.

In examples, the standard electromechanical time interval range comprises a range of about 80 ms to about 150 ms. In some examples, the standard electromechanical time interval range can comprise a range of about 100 ms to about 140 ms. In some examples, the standard electromechanical time interval range can comprise a range of about 110 ms to about 130 ms. In examples, the standard electromechanical time interval range can comprise a range that spans at least one of at least 10 ms, at least 15 ms, at least 20 ms, at least 30 ms, at least 40 ms, at least 50 ms, at least 60 ms and at least 70 ms within the range of about 80 ms to about 150 ms. In examples, the standard time electromechanical interval range includes at least one of 80 ms-85 ms, 85 ms-90 ms, 90 ms-95 ms, 95 ms-100 ms, 100 ms-105 ms, 105 ms-110 ms, 110 ms-115 ms, and 115 ms-120 ms, 120 ms-125 ms, 125 ms-130 ms, 130 ms-135 ms, 135 ms-140 ms, 140 ms-145 ms, and 145 ms-150 ms. In examples, the at least one processor can be configured to provide the output based on the comparison when the at least one time interval falls outside of a range of within at least one of: 1% of the standard electromechanical time interval, 2% of the standard electromechanical time interval, 5% of the standard electromechanical time interval, 10% of the standard electromechanical time interval, 15% of the standard electromechanical time interval, and 20% of the standard electromechanical time interval. The at least one processor can be configured to identify an improving or worsening heart failure condition of the patient based on the output. In examples, the device further includes a network interface configured to transmit the output to a remote server.

In examples, the at least one processor is configured to compare the at least one electromechanical time interval with a subsequent electromechanical time interval representing a subsequently monitored cardiac cycle during a subsequent patient activity, provide an output based on the comparison, and determine an improving or worsening heart failure condition of the patient based on the output. In some examples, the device further includes a network interface configured to transmit the output to a remote server.

In examples, the at least one electromechanical time interval includes a plurality of electromechanical time intervals measured during a plurality of patient activities. The at least one processor can be configured to monitor for one or more trends in the plurality of electromechanical time intervals, and display an output based on the one or more trends. The device can further include a network interface configured to transmit the output to a remote server. In examples, the at least one processor is further configured to determine an improving or worsening heart failure condition of the patient based on the output.

In examples, the at least one electromechanical time interval is indicative of systolic function of the patient's heart.

In examples, the at least one processor is further configured to determine that the patient is engaged in the patient activity based on detecting a predetermined elevation in a heart rate derived from an ECG signal of the patient, and store a activity start marker in a memory of the device on determining that the patient is engaged in the patient activity. In some examples, the predetermined elevation of the heart rate is an elevation of at least between 5-20% of a baseline or standard heart rate of the patient. In some examples, the predetermined elevation of the heart rate is over a duration of at least between 1 to 5 minutes. In examples, the at least one processor is configured to prompt the patient to confirm that the patient is engaged in the patient activity prior to storing the activity start marker in the memory. The at least one processor can be configured to determine that the patient is engaged in the patient activity further based on signals from the activity sensor indicating patient movements.

In examples, the at least one processor is further configured to measure, during the patient activity, a cardio-vibrational time interval measured from a first cardio-vibrational fiducial point of an S1 cardio-vibrational biomarker to a second cardio-vibrational fiducial point of an S2 cardio-vibrational biomarker for the cardiac cycle. In some examples, the cardio-vibrational time interval includes a left ventricular systolic time (LVST) interval.

In examples, the at least one processor is further configured to measure, during the patient activity, a S3 cardio-vibrational biomarker strength derived from the cardio-vibrational signal.

In examples, the device includes a wearable defibrillator including a garment configured to be worn about the torso of the patient, and at least two therapy electrodes supported by the garment and configured to deliver energy to the torso of the patient. In examples, the at least one physiological sensor is supported by the garment. The device can be configured to be worn for a prescribed period of wear of at least between one week and two weeks, two weeks and one month, one month and two months, two months and three months, and three months and six months.

In some examples of the device, the vibrational sensor includes the activity sensor.

In examples, the patient activity has an activity duration of between at least 3 to 6 minutes, between at least 6 to 12 minutes, between at least 12 to 15 minutes, between at least 15 to 20 minutes, between at least 20 to 30 minutes, between at least 30 to 45 minutes, and between at least 45 minutes to an hour.

In some examples, the device is configured to prompt the patient to engage in the patient activity. The patient activity can be a prescribed activity prompted at scheduled intervals. In examples, a network interface is configured to communicate with a remote server, and the remote server is configured to transmit an instruction to the device via the network interface to prompt the patient to initiate the patient activity.

In examples, the device further includes a user interface configured to guide the patient through the patient activity.

In examples, the at least one electromechanical time interval begins from an ECG fiducial comprising at least one of a point on a P-wave segment of the ECG signal, a point on a P-Q segment of the ECG signal, point on a Q-wave segment of the ECG signal, a point on an R-wave segment of the ECG signal, a point at the beginning of the R-wave segment, and ends at the cardio-vibrational fiducial point. In examples, the cardio-vibrational fiducial point occurs within an S1 cardio-vibrational biomarker of the cardio-vibrational signal.

In examples, the at least one processor can be configured to measure an RR interval of the ECG signal and calculate a ratio of the at least one electromechanical time interval to the RR interval.

In examples, the at least one electromechanical time interval begins from the cardio-vibrational fiducial point within an S2 cardio-vibrational biomarker of the cardio-vibrational signal and the ECG fiducial point at an onset of a next Q wave in the ECG signal.

In examples, the at least one electromechanical time interval includes an LDPT interval.

In examples, the at least one electromechanical time interval includes an electromechanical activation time (EMAT) interval.

In some examples, the at least one processor can be configured to calculate a ratio of at least one of a: EMAT/LVST, EMAT/LDPT, and EMAT/RR.

In examples, initiation of the patient activity is determined based on at least one of the heart rate information from the heart rate sensor and the monitored patient movements from the activity sensor. In examples, the heart rate sensor includes an ECG sensor and the heart rate of the patient is calculated from the ECG signals of the ECG sensor.

In examples, initiation of the patient activity is determined based on a patient input to the device.

The details of one or more implementations of the subject matter described in this specification are set forth in the accompanying drawings and the description. Other features and advantages will be apparent from the description, drawings, and the claims. In the figures, each identical or nearly identical component that is illustrated in various figures is represented by a like numeral. For purposes of clarity, not every component may be labeled in every figure.

BRIEF DESCRIPTION OF THE DRAWINGS

FIGS. 12A-E depict example user interface screens for engaging in a patient activity.

FIGS. 13A-E depict example user interface screens for confirming engagement in detected patient activity.

FIGS. 14A-C depict example user interface screens of a patient-worn medical device for displaying example output.

DETAILED DESCRIPTION

Figure 1:
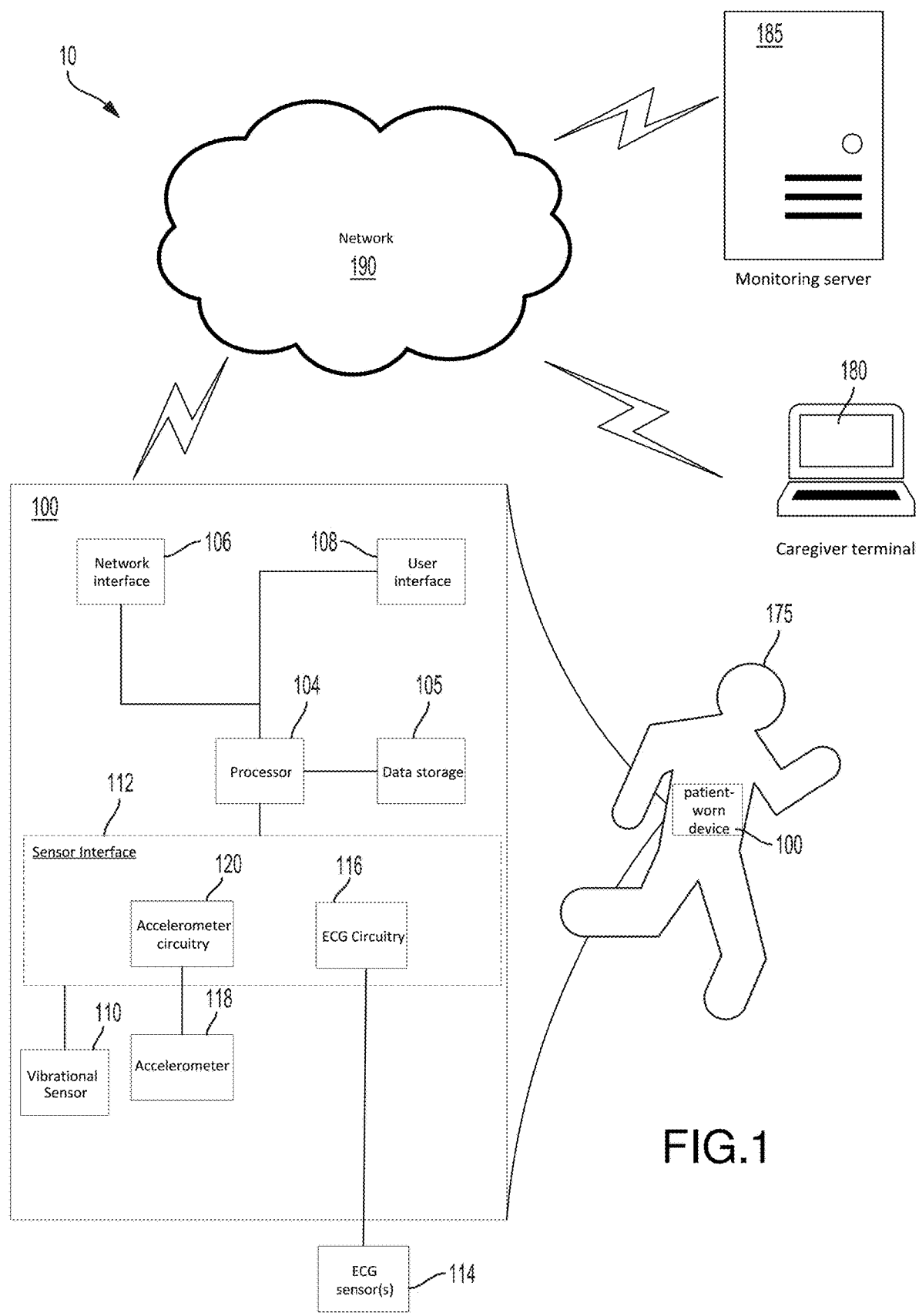
FIG. 1 depicts an example system for monitoring physiological changes during periods of activity.

Heart failure patients can be prescribed a cardiac monitoring device or a cardiac monitoring and treatment device. In some cases, physicians may use medical devices alone or in combination with drug therapies to treat heart failure conditions. Depending on the underlying condition being monitored or treated, medical devices such as cardiac monitors or defibrillators may be surgically implanted or externally connected to the patient. In some examples, the cardiac monitoring device may be an external wearable cardiac device for ambulatory use. Wearable medical devices, such as cardiac event monitoring devices, are used in clinical or outpatient settings to monitor and record various physiological signals for a patient. In some examples, a wearable cardiac monitoring and treatment device may be a wearable defibrillator. This disclosure generally relates to wearable cardiac devices for monitoring patients engaged in physical activities. Exemplary devices, systems, and methods for managing patient care by monitoring physiological status during physical activity are now described in more detail.

In some implementations, a patient-worn ambulatory cardiac monitoring device for monitoring a patient during a patient activity includes sensors configured to detect one or more physiological signals of the patient. Such physiological sensors may include at least one physiological sensor configured to monitor signals indicative of cardiac activity, such as ECG signals and/or heart rate of the patient. For example, such ECG sensors can include one or more ECG electrodes configured to be in contact with the patient. The ECG electrodes can be placed in contact with the patient's skin, for example, on the torso of the patient. In some examples, the one or more ECG electrodes are a plurality of ECG sensors in contact with a torso of the patient and configured to monitor an ECG signal of the patient. Physiological sensors configured to monitor signals indicative of cardiac activity can also include heart rate sensors. The heart rate sensors may include sensors that are used alone or in combination such as, for example, the ECG sensors, pulse oximetry sensors, vibrational sensors including cardio-vibrational sensors, and/or radio frequency-based arterial pulse sensors. Additionally, the cardiac monitoring device includes at least one sensor configured to monitor the patient's movements during a physical activity, such as walking, jogging, cycling, or other activities elevating heart rate. Such movement monitoring sensors may include, for example, an accelerometer, a gyroscope, a 3-axis inertial measurement unit (IMU), a 6-axis IMU, a magnetometer, an altimeter, and associated circuitry for one or a combination of such sensors. For instance, such a movement sensor (or activity sensor) may include an accelerometer and associated circuitry.

Additionally, the cardiac monitoring device includes at least one sensor for monitoring a cardio-vibrational signal of the patient. For example, such a sensor may include a vibrational sensor configured to monitor a cardio-vibrational signal of the patient. In implementations, the device includes at least one processor in communication with the at least one heart rate and/or ECG sensor, the accelerometer, and the vibrational sensor. The processor can be configured to measure, during the patient activity, at least one time interval between an ECG fiducial point on the ECG signal and a cardio-vibrational fiducial point on the cardio-vibrational signal during a cardiac cycle of the patient's heart.

In some implementations, the at least one time interval can be an electromechanical activation time (EMAT) interval. In some implementations, the at least one time interval can be a left ventricular diastolic perfusion time (LDPT) interval. Because EMAT is indicative of a systolic time interval and LDPT is indicative of a diastolic time interval, monitoring these time intervals for changes during periods of activity during which a patient's heart rate is elevated provides an indication as to improving or worsening heart failure. An indication of a worsening heart failure condition can highlight for a caregiver that a prescribed treatment may need modification. Such monitoring can assist with predictive and preventative decompensation and hospitalization of a patient. Accordingly, such devices can assist with predicting recovery results stemming from early detection and intervention for a worsening condition.

Additionally or alternatively, the processor can measure, during the patient activity, a cardio-vibrational strength of a cardio-vibrational biomarker. The cardio-vibrational strength can be representative of an S3 cardio-vibrational biomarker intensity, timing within the cardiac cycle, frequency, and persistence. For example, an increased intensity, frequency, and/or persistence of the S3 cardio-vibrational biomarker over a plurality of cardiac cycles (e.g., 10 heart beats, 100 heartbeats, 1000 heartbeats, or more) can indicate worsening diastolic function.

Further, the processor can measure, during the patient activity, a cardio-vibrational interval from a first cardio-vibrational fiducial point to a second cardio-vibrational fiducial point in the cardio-vibrational signal during a cardiac cycle of the patient's heart. For example, the first cardio-vibrational fiducial point can be within a first cardio-vibrational biomarker of the cardio-vibrational signal (e.g., the S1 cardio-vibrational biomarker) and the second cardio-vibrational fiducial point can be within a second cardio-vibrational biomarker (e.g., the S2 cardio-vibrational biomarker) of the cardio-vibrational signal. For example, such a cardio-vibrational interval can represent the left ventricular systolic time (LVST) interval.

In implementations, the device may compare the at least one cardio-vibrational interval to a baseline or standard cardio-vibrational interval and determine if the patient is experiencing an improving or worsening heart failure condition. Because LVST is indicative of a systolic time interval, monitoring this time interval for changes during periods of activity during which a patient's heart rate is elevated provides an indication as to improving or worsening heart failure. An indication of a worsening heart failure condition highlights for a caregiver that a prescribed treatment is not working and may need modification.

The physiological data collected during patient activity as described above can be analyzed to provide feedback for caregivers in administering heart failure care. Such analysis can involve one or more of comparing the electromechanical time interval, the cardio-vibrational strength, and/or the cardio-vibrational time interval values to one or more baseline values or one or more standard values or ranges. The analysis can also include monitoring trends of these values over a period of time. In one implementation, the processor of the cardiac monitoring and/or treatment device is configured to analyze the physiological data collected during patient activity as described above. In an example, the physiological data can be stored in a memory on the device, and some or all of the analysis can be performed once the device is returned to a service center and the physiological data downloaded from the device to a computer system. In some examples, the physiological data can be transmitted over a network via a network interface on the device for analysis at the service center. For example, the device can transmit the physiological data substantially immediately following a patient activity and/or after recording the physiological data (e.g., within 1-2 seconds, 10-20 seconds, 1-5 minutes, 5-30 minutes, 30 minutes to an hour, 1-2 hours, 2-24 hours, or another user-defined and/or preconfigured duration).

Turning now to FIG. 1, in one implementation, a cardiac monitoring system 10 for monitoring physiological changes in a patient 175 during periods of activity includes a wearable medical device 100 in wired or wireless communication with a remote monitoring server 185. The device 100 can be a patient-worn ambulatory cardiac monitoring and/or treatment device. In implementations, the device 100 is in wireless communication with the server 185 and includes a network interface 106 for transmitting data over a wireless link such as a Bluetooth® wireless link (e.g., via a "hotspot", base station, or other intermediate device), a broadband cellular link, or a Wi-Fi™ communications link based on the IEEE 802.11 standard. A caregiver terminal 180 and the wearable medical device 100 can be operably connected to the remote server 185 through a communication network 190. In certain implementations, while being worn, the device 100 collects information related to the patient 175 such as various physiological conditions as described herein. Depending upon the status of a connection to the communication network 190 and the programmed instructions of the device 100, the device 100 can be configured to regularly transmit the collected information to the server 185 for further processing. For example, the server 185 can be configured to monitor the physiological status of a patient 175 based on patient data obtained from multiple sensors. In implementations, the sensors include bio-vibrational sensors (e.g., vibrational sensors 110) and one or more ECG sensors 114, and the data is transmitted to the server 185 by, for example, one or more devices 100. In some examples, one or more physicians, other caregivers, patient care representatives, or other authorized users, can access the patient status information using the caregiver terminal 180 to review changes in patient condition, input an instruction or recommendation to change a patient's treatment regimen, and to perform other similar patient care functions.

In implementations, the device 100 includes at least one processor 104, data storage 105, a network interface 106, a user interface 108, and a sensor interface 112. The sensor interface 112 connects one or more sensors with the processor 104. In implementations, the one or more sensors include an accelerometer 118, the ECG sensors 114, and at least one vibrational sensor 110.

The data storage 105 can include one or more of non-transitory computer readable media, such as flash memory, solid state memory, magnetic memory, optical memory, cache memory, combinations thereof, and others. The data storage 105 can be configured to store executable instructions and data used for operation of the device 100. In certain implementations, the data storage 105 can include executable instructions that, when executed, are configured to cause the processor 104 to perform one or more functions.

In some examples, the network interface 106 can facilitate the communication of information between the device 100 and one or more other devices or entities over a communication network 190. In an example, the device 100 is an ambulatory medical device, and the network interface 106 can be configured to communicate output with remote computing devices such as a remote server 185 and caregiver terminal 180. The network interface 106 can include communications circuitry for transmitting data in accordance with a Bluetooth® wireless standard for exchanging such data over short distances to an intermediary device(s), e.g., base station, "hotspot" device, smartphone, tablet, portable computing device, and/or other devices in proximity of the wearable medical device. For example, such communications circuitry can be a Bluetooth® network adapter. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server 185 over a Wi-Fi™ communications link based on the IEEE 802.11 standard.

In certain implementations, the user interface 108 can include one or more physical interface devices such as input devices, output devices, and combination input/output devices, and associated encoded instructions configured to drive operation of these devices. These user interface devices may render visual, audio, and/or tactile content. Thus the user interface 108 may receive input or provide output, thereby enabling a user, such as the patient 175, to interact with the device 100. For example, the user interface 108 can include one or a combination of a screen display, a touch screen display, LED and/or LCD display, LED lights, physical buttons, soft buttons (e.g., touch fields on a screen), one or more speakers, and/or one or more microphones.

The sensor interface 112 can be coupled to one or more sensors configured to monitor one or more physiological parameters of the patient 175. As shown, the sensors, can be coupled to the medical device 100 via a wired or wireless connection. The sensors can include one or more electrocardiogram (ECG) sensors 114, e.g., ECG electrodes, one or more vibrational sensors 110, and a patient movement sensor, e.g., an accelerometer 118, a gyroscope, a magnetometer, an altimeter, a 3-axis IMU, and/or a six-axis IMU.

The one or more ECG sensors 114 can monitor a patient's ECG information. For example, the ECG sensors 114 can be non-polarizable ECG electrodes (e.g., clinical grade Ag/AgCl electrodes) or polarizable electrodes (e.g., electrodes having a metal substrate with an oxide layer, such as a $Ta_2O_5$ coating) configured to measure changes in a patient's electrophysiology to measure the patient's ECG information. The one or more ECG sensors 114 can transmit information descriptive of the ECG signals to the sensor interface 112 via ECG circuitry 116 for subsequent analysis.

The vibrational sensor 110 can detect a patient's vibrations associated with, for example, heart and lung activity. For example, the vibrational sensor 110 can be a cardio-vibrational sensor configured to detect cardio-vibrational biomarkers including any one or all of S1, S2, S3, and S4 cardio-vibrational biomarkers. The system 10 can determine physiologic characteristics from these cardio-vibrational biomarkers, including at least one of electromechanical activation time (EMAT) interval, left ventricular systolic time (LVST) interval, percentage of left ventricular systolic time (% LVST), left ventricular diastolic perfusion time (LDPT) interval, EMAT/RR, EMAT/LDPT, and LVST/LDPT. In implementations, the one or more vibrational sensors 110 includes a multi-channel accelerometer, for example, a three channel accelerometer (e.g., 3-axis IMU) configured to sense movement in each of three orthogonal axes such that patient movement/body position can be detected and correlated to detected heart vibrations information. The one or more vibrational sensors 110 can transmit information descriptive of the cardio-vibration information to the sensor interface 112 for subsequent analysis.

The patient movement sensor can include one or more accelerometers 118 configured to measure motion data related to patient movement. In some implementations, the accelerometer 118 can be coupled to accelerometer circuitry 120 and processor 104 that is configured to receive the accelerometer signals from the circuitry 120 and measure the number of steps a patient takes over a particular amount of time. For example, a patient can be instructed to perform a particular exercise such as a walking activity. For example, such a walking activity can be a 6-minute walk test, a sub-maximal exercise test generally used to assess aerobic capacity and endurance. The patient movement sensor, such as the accelerometer 118, and associated accelerometer circuitry 120 and processor 104 can be configured to measure step, pace and/or distance covered during the particular exercise. In some implementations, the one or more accelerometers 118 can be integrated into other components such as the one or more vibrational sensors 110. Alternatively, the vibrational sensors 110, in some implementations, can perform one or more functions of the patient movement sensors as described herein.

In some implementations, the processor 104 includes one or more processors (or one or more processor cores) that each are configured to perform a series of instructions that result in manipulated data and/or that control the operation of the device 100. In some implementations, when executing a specific process (e.g., cardiac monitoring), the processor 104 can be configured to make specific logic-based determinations based on input data received from the one or more sensors. The processor 104 can be further configured to provide one or more outputs that can be used to control or otherwise inform subsequent processing to be carried out by the processor 104 and/or other processors or circuitry with which processor 104 is communicatively coupled, such as, for example, the remote server 185 and the caregiver terminal 180. Thus, the processor 104 reacts to specific input stimulus in a specific way and generates a corresponding output based on that input stimulus.

Figure 2:
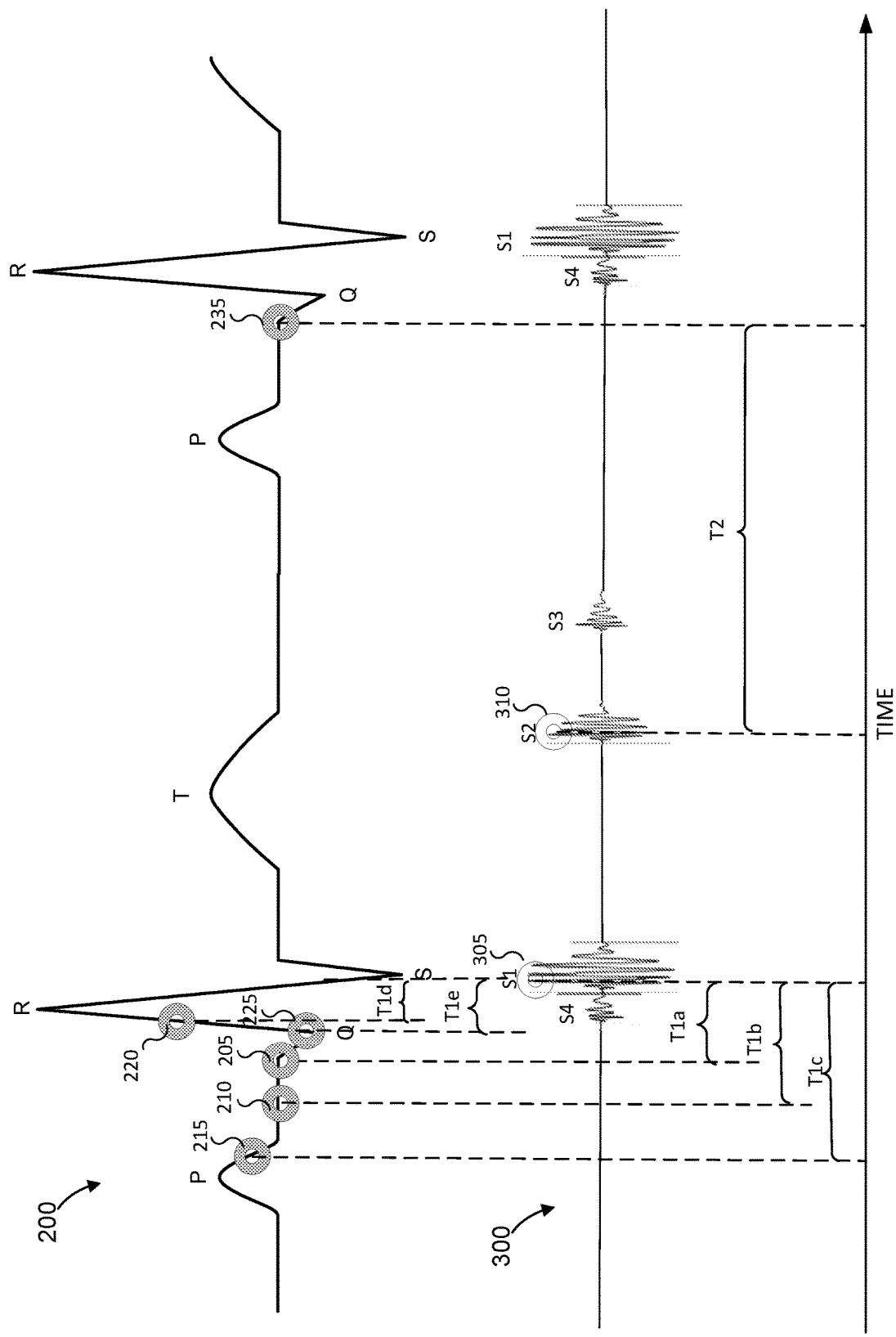
FIG. 2 depicts example electromechanical time intervals and cardio-vibrational signals for cardiac cycles.
Figure 3:
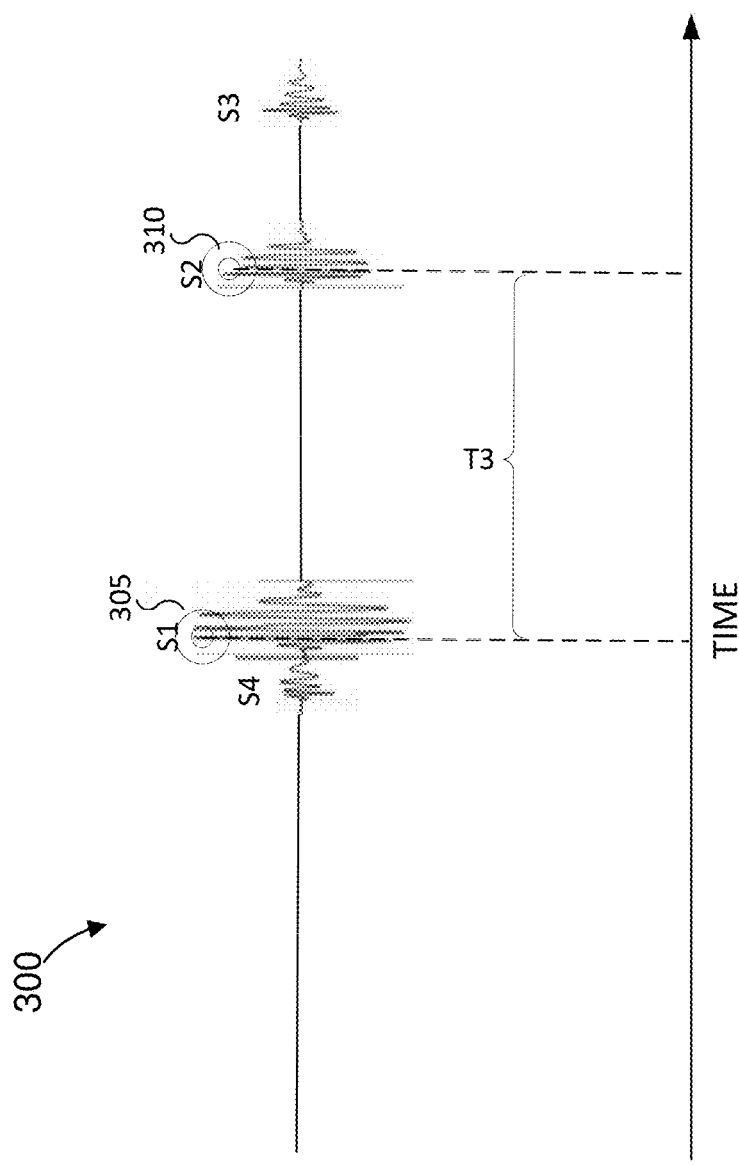
FIG. 3 depicts example cardio-vibrational biomarkers for a cardio-vibrational signal of a cardiac cycle.

Referring now to FIGS. 2 and 3, an ECG signal 200 and a cardio-vibration signal 300 that emanates from a heart of a patient and the resultant flow of blood through the patient's heart are shown. For example, one or more vibrational sensors (such as the vibrational sensor 110 of FIG. 1) can be used to detect distinct cardio-vibrational biomarkers that provide insight into how well a patient's heart is functioning.

In healthy hearts, a cardio-vibrational signal 300 includes at least two normal heart vibrations, often described as a lub and a dub (or dup). The heart vibrations occur in sequence with each heartbeat in a cardiac cycle, as shown in connection with the ECG signal 200. For example, a cardio-vibrational signal 300 includes a first cardio-vibrational biomarker, the S1 cardio-vibrational biomarker (hereinafter referred to interchangeably as "S1"), and a second cardio-vibrational biomarker, the S2 cardio-vibrational biomarker (hereinafter referred to interchangeably as "S2"). The S1 cardio-vibrational biomarker is produced by the closing of the atrioventricular valves (AV valves) and the S2 cardio-vibrational biomarker is produced by closing of the semilunar valves (SL valves). More specifically, the S1 cardio-vibrational biomarker represents the closing of the AV valves including the tricuspid valve positioned between the right atria and right ventricle and the mitral valve located between the left atria and left ventricle. The S2 cardio-vibrational biomarker represents the closing of the SL valves including the pulmonic valve that ejects blood to the lungs to get oxygen and is positioned between the right ventricle and the pulmonary artery, and the aortic valve that ejects oxygenated blood to the body and is positioned between the left ventricle and the aorta.

In addition to S1 and S2 cardio-vibrational biomarkers, S3 and S4 cardio-vibrational biomarkers can be picked up by vibrational sensors 110. The S3 cardio-vibrational biomarker is a cardio-vibration that occurs soon after the normal two "lub-dub" cardio-vibrational biomarkers (S1 and S2). The S3 cardio-vibrational biomarker typically occurs at the beginning of the middle third of diastole during passive filling of the ventricles. The S3 cardio-vibrational biomarker can be associated with heart failure, for example as a result of the vibration of blood hitting the walls of the ventricles which may be stiffer in a patient suffering from cardiac problems. For example, in monitoring systems described here, the S3 cardio-vibrational biomarker can be monitored to detect possible cardiac problems, such as a failing left ventricle as in dilated congestive heart failure (CHF).

Systems and methods disclosed can be configured to detect characteristics of the S3 vibration. For example, a sensitive vibrational sensor 110 configured to detect the S3 cardio-vibrational biomarker can provide a value of strength of the vibration in the range of 0 to 10 (e.g., 0 to 10 strength units).

In implementations, strength of a cardio-vibrational biomarker can be based on a peak intensity of the biomarker multiplied by the corresponding duration. In implementations, strength of the cardio-vibrational biomarker can be a function of one or more of the intensity of the biomarker, a timing of the biomarker within a cardiac cycle, a frequency, and/or persistence of the biomarker. In implementations, such persistence can be the appearance of the cardio-vibrational biomarker within consecutive cardio-vibrational signals 300, for example, 5 or more cardio-vibrational signal cycles, 10 or more cardio-vibrational signal cycles, 20 or more cardio-vibrational signal cycles, and 30 or more cardio-vibrational signal cycles, 50 or more cardio-vibrational signal cycles, 100 or more cardio-vibrational signal cycles, 200 or more cardio-vibrational signal cycles, 500 or more cardio-vibrational signal cycles, and 1000 or more cardio-vibrational signal cycles. By analyzing a pattern of persistence of an observed cardio-vibrational biomarker over a number of cardiac cycles (e.g., heart beats), a determination can be made as to the persistence of the observed cardio-vibrational biomarker.

An increased and/or persistent S3 cardio-vibrational biomarker indicates impaired and/or worsening diastolic function. For example, this can indicate the presence of one or more conditions such as hypertension, diabetes, coronary artery disease, and non-ischemic cardiomyopathy.

The vibrational sensor 110 can be configured to detect and monitor biovibrations other than cardio-vibrations, such as, lung vibrations, breathing/chest wall movements, sleep related parameters (e.g., snoring, sleep apnea), and other such bio-vibrations. In an implementation, the vibrational sensor 110 can include a high fidelity diaphragm, e.g., a dynamic, electret condenser, ribbon based, or a piezoelectric crystal based diaphragm. Separately, a plurality of motion sensors (e.g., at least two, four, six, or more) can be located around a periphery of the diaphragm. The vibrational signals from the diaphragm and the plurality of motion sensors can be digitized by a series of analog to digital converters (ADC) and processed through a digital signal processing unit. For example, the digital signal processing unit can include a series of digital filters. For example, the vibrational sensor 110 can include multi-axial accelerometers that produce digitized signals that are input to the digital signal processing unit along with the digitized diaphragm signal. The signals from one or more of the plurality of motion sensors can be used to monitor low frequency vibrations. For example, such low frequency vibrations comprise breathing and/or chest wall movement.

As described above with regard to the system 10 of FIG. 1, in some implementations, a patient-worn ambulatory cardiac monitoring device 100 for monitoring a patient during a patient activity includes sensors configured to detect one or more physiological signals of the patient 175. In implementations, the processor 104 is configured to measure, during the patient activity, at least one electromechanical time interval. For example, the processor 104 can be configured to measure at least one time interval between an ECG fiducial point on the ECG signal 200 and a cardio-vibrational fiducial point on the cardio-vibrational signal 300 during a cardiac cycle of the patient's heart.

Turning back to FIGS. 2 and 3, example electromechanical time intervals are shown as T1*a*, T1*b*, T1*c*, T1*d*, and T1*e*. In some implementations, a time interval Tia begins from when the ECG fiducial point 205 is on a Q-wave segment of the ECG signal 200 and ends at the cardio-vibrational fiducial point 305 within an S1 cardio-vibrational biomarker of the cardio-vibrational signal 300. In implementations, the time interval T1*b* begins from when the ECG fiducial point 210 is on a P-Q segment of the ECG signal 200 and ends at the cardio-vibrational fiducial point 305 within an S1 cardio-vibrational biomarker of the cardio-vibrational signal 300. In implementations, the time interval T1*c* begins from when the ECG fiducial point 215 is on a P-wave segment of the ECG signal 200 and ends at the cardio-vibrational fiducial point 305 within an S1 cardio-vibrational biomarker of the cardio-vibrational signal 300.

In examples, the time interval T1*d* can begin from when the ECG fiducial point 220 is on an R-wave segment and end at a cardio-vibrational fiducial point 305 within an S1 cardio-vibrational biomarker of the cardio-vibrational signal. In some examples, the at least one time interval T1*e* can begin from when the ECG fiducial point 225 is at the beginning of the R-wave segment and ends at the cardio-vibrational fiducial point 305 within the S1 cardio-vibrational biomarker of the cardio-vibrational signal.

In implementations, the S1 cardio-vibrational fiducial point 305 can be located anywhere within the S1 cardio-vibrational biomarker, at the start of the S1 cardio-vibrational biomarker, at the end of the S1 cardio-vibrational biomarker, or at the peak amplitude of the S1 cardio-vibrational biomarker in the cardio-vibrational signal 300.

In implementations, the processor 104 is configured to measure an RR interval of the ECG signal 200. The processor 104 can then calculate a ratio of the electromechanical time interval, as calculated above, to the RR interval. The processor can also calculate a ratio of the electromechanical time interval to a time interval T2 as shown in FIG. 2. The time interval T2 is the left ventricular diastolic perfusion time (LDPT). The time interval T2 is between a cardio-vibrational fiducial point 310 within an S2 cardio-vibrational biomarker of the cardio-vibrational signal 300 and the ECG fiducial point 235 at an onset of a next Q wave in the ECG signal 200. The S2 cardio-vibrational fiducial point 310 can be located anywhere within the S2 cardio-vibrational biomarker, at the start of the S2 cardio-vibrational biomarker, at the end of the S2 cardio-vibrational biomarker, or at the peak amplitude of the S2 cardio-vibrational biomarker in the cardio-vibrational signal 300. Further, the processor can also calculate a ratio of the electromechanical time interval to an LVST of the patient.

In implementations, the electromechanical time interval can be an electromechanical activation time (EMAT), and the at least one processor can be configured to calculate a ratio of at least one of a: EMAT/LVST, EMAT/LDPT, and EMAT/RR as described above.

Turning now to FIGS. 4 through 8, example methods for monitoring physiological status of a patient during physical activity include baseline comparison, standard comparison, and trend analysis.

Figure 4:
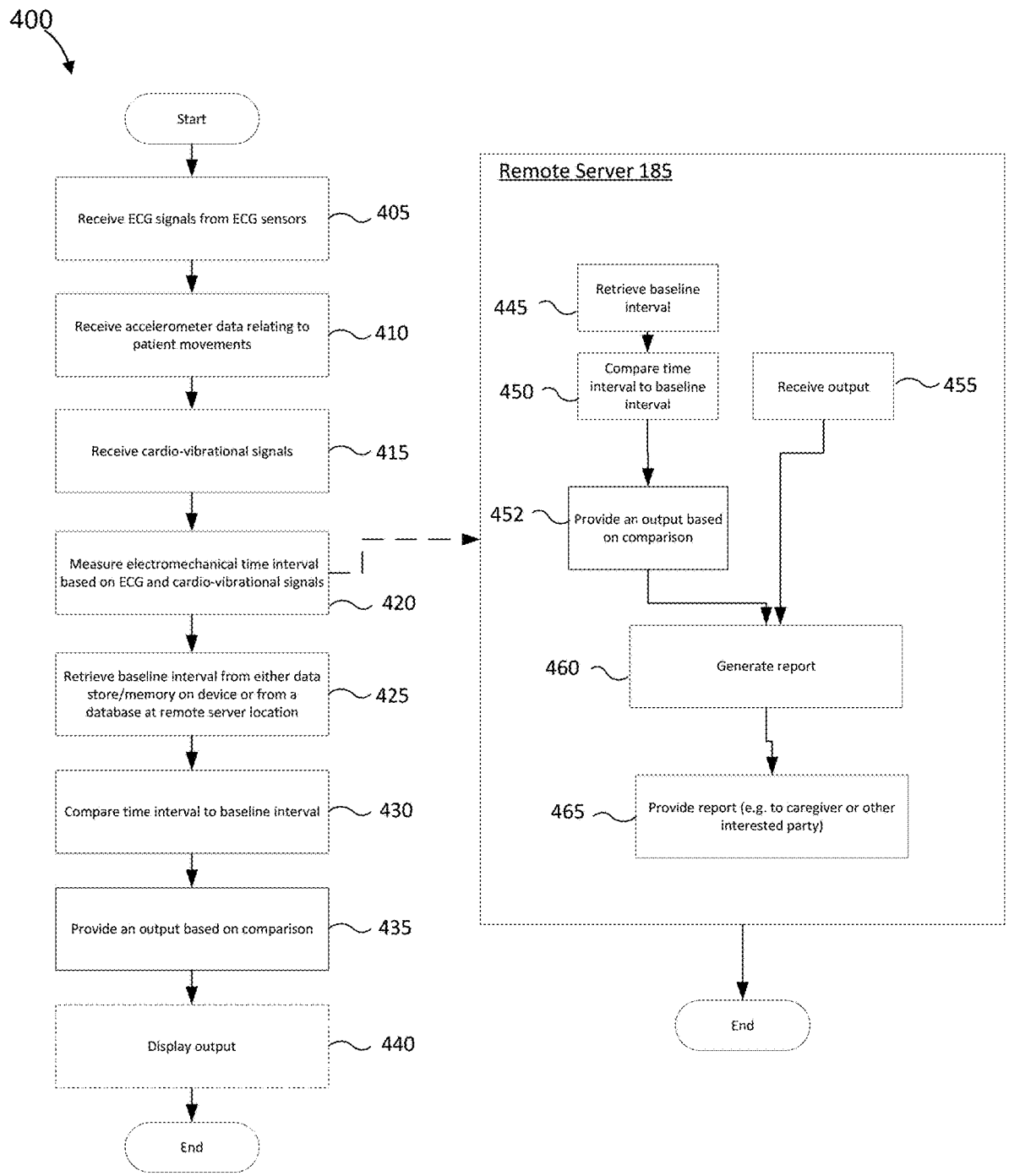
FIG. 4 depicts example methods for identifying physiological conditions.
Figure 5:
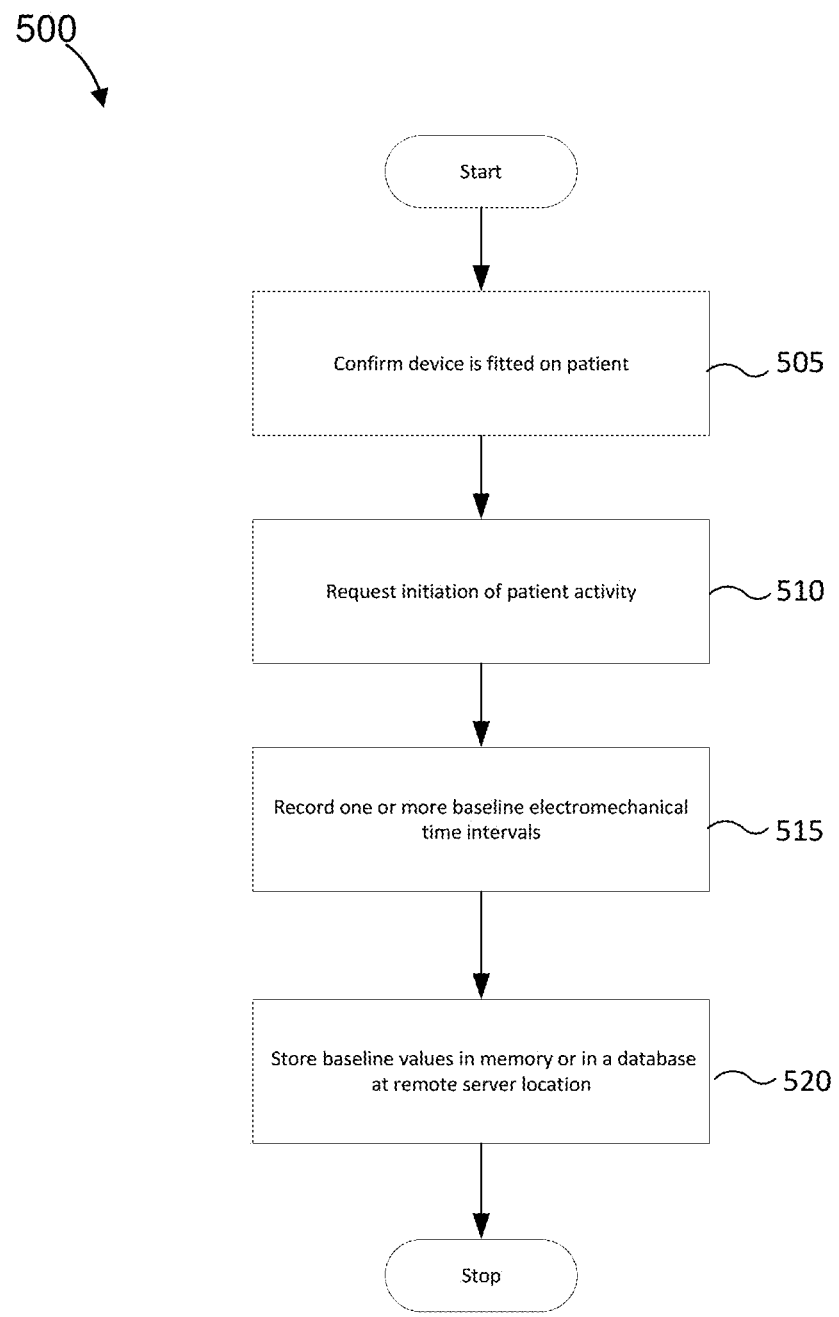
FIG. 5 depicts example methods for baselining a physiological response.

For example, FIGS. 4-5 demonstrate example methods of comparing 400 the at least one electromechanical time interval to a baseline time interval and a method of recording 500 the baseline interval. As shown in FIG. 4, the device 100 receives 405 ECG signals from the at least one ECG sensor 114, receives 410 accelerometer data from the accelerometer 118 related to patient movements, and receives 415 cardio-vibrational signals from the vibrational sensor 110. The processor 104 is configured to measure 420 a time interval based on the ECG signal and the cardio-vibrational signal. For example, as described above, in one implementation the processor 104 is configured to measure, during patient activity, at least one electromechanical time interval (e.g., T1*a*, T1*b*, T1*c*, T1*d*, or T1*e*) between an ECG fiducial point and a cardio-vibrational fiducial point (e.g., an S1 cardio-vibrational biomarker) during one or more cardiac cycles of the patient's heart.

The processor is then configured to retrieve 425 a baseline interval from a data storage 105 or memory on the device 100 or from a database at a remote server location (e.g., server 185 of the exemplary system 10 of FIG. 1).

Turning to FIG. 5, an example method for recording 500 a baseline time interval includes confirming 505 that the device 100 is fitted on the patient. This can be done automatically by the device 100 monitoring signals for proper contact between one or more sensors and the torso of the patient. Alternatively or additionally, a patient service representative, physician, or other caregiver may visually inspect for proper fit and/or run a diagnostic test for proper fit on the patient.

With the device properly fitted on the patient, the method of recording 500 a baseline time interval includes requesting 510 initiation of patient activity. The processor 104 of the device 100 may automatically run a baseline script that automatically prompts the patient 175 to begin an activity, such as walking for a prescribed duration. The prompt can be, for example, an audible, tactile (e.g., vibration) and/or visual indication on the user interface 108 of the device 100 or a handheld device in wireless communication with the device 100, such as a smart phone, smart watch, or other computing device with audio circuitry and/or a user interface. Alternatively, the patient or a patient service representative, physician, or other caregiver may indicate to the device 100 an initiation of activity by pressing a button or a touchscreen soft button of the device 100 or a remote control device in communication with the device 100. Such remote control devices may include, for example, a smart phone, smart watch, or other computing device in communication with the device 100 and configured to send data and/or instructions to the device 100.

The processor 104 is configured to record 515 one or more baseline time intervals and store 520 the baseline time interval(s) in a data storage 105 or memory on the device 100 or from a database at a remote server location (e.g., server 185 of the exemplary system 10 of FIG. 1).

Turning back to FIG. 4, once the baseline time interval is retrieved 425 from a local data storage 105 or a remote database, the processor 104 is configured to compare 430 the at least one time interval to the retrieved baseline time interval and provide 435 an output based on the comparison. As will be described subsequently with regard to FIGS. 14A-C, in some implementations, the processor 104 configures the device 100 to display 440 the output on the user interface 108 and/or communicates with a user device (e.g., a smart phone, smart watch, or other computing device) in communication with the device 100 to display the output. In implementations, the processor 104 is configured to provide the output based on the comparison when the at least one time interval falls outside of a range of within at least one of one percent of the baseline time interval, two percent of the baseline time interval, five percent of the baseline time interval, ten percent of the baseline time interval, fifteen percent of the baseline time interval, and twenty percent of the baseline time interval.

In some implementations, the device 100 provides sensor data to the remote server 185. A processor of the remote server retrieves 445 the baseline time interval and compares 450 the at least one time interval to the baseline interval, provides 452 an output based on the comparison, and generates 460 a report. The server 185 then provides 465 the report to a physician, other caregiver, patient service representative, or other authorized party in communication with the remote server via a caregiver terminal 180, for example. The reports can be provided automatically upon generation or upon request by the end user. In another implementation, the remote server 185 receives 455 the output provided by network interface 106 of the device 100. The server 185 generates 460 a report and provides 465 the report to a physician, other caregiver, patient service representative, or other interested party. Example reports will be described subsequently with regard to FIG. 15. In some implementations, the processor 104 of the device or a processor of the remote server 185 is configured to identify an improving or worsening heart failure condition of the patient based on the output. Additionally or alternatively, the output displayed on the user device 100 or provided in a report enables a patient, physician, other caregiver, patient service representative, or other user to evaluate the monitored physiological data of the patient 175 and identify an improving or worsening condition.

Figure 6:
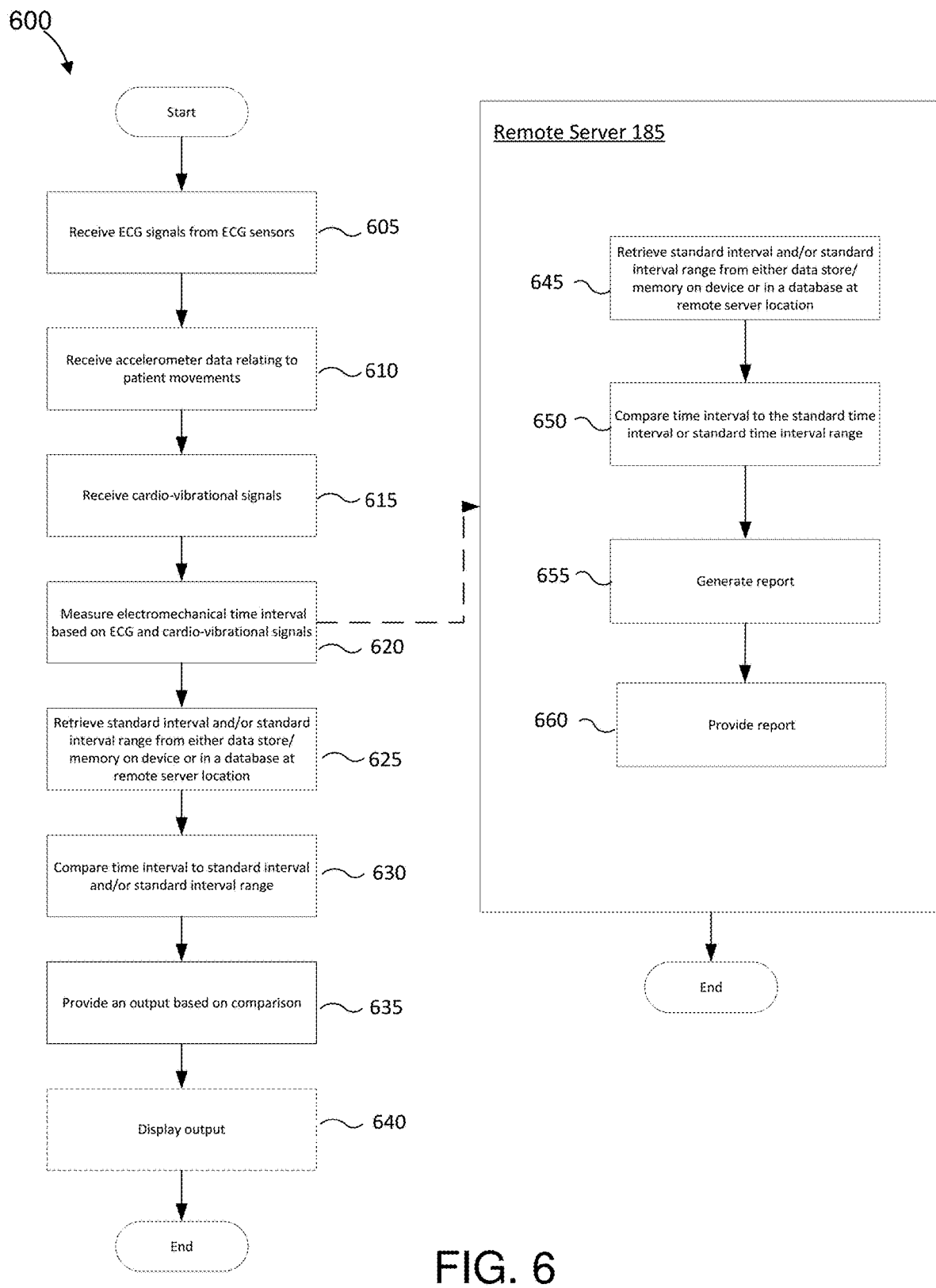
FIG. 6 depicts example methods for identifying physiological conditions.

Turning now to FIG. 6, in addition to or alternatively to comparing the at least one time interval to a baseline time interval, the processor 104 of the device 100 can be configured to compare the at least one time interval to a standard time interval. In another example, the processor 104 of the device 100 can be configured to compare the at least one time interval to a standard time interval range, verifying whether the at least one time interval falls within the standard time interval range. In implementations, a method of comparing 600 the at least one time interval to a standard time interval or standard time interval range includes receiving 605 ECG signals from the at least one ECG sensor 114, receiving 610 accelerometer data from the accelerometer 118 related to patient movements, and receiving 615 cardio-vibrational signals from the vibrational sensor 110. In one example, the processor 104 of the device 100 is configured to measure 620 at least one electromechanical time interval based on the ECG signal and the cardio-vibrational signal. For example, the method of comparing 600 can include measuring at least one time interval between an ECG fiducial point on the ECG signal and a cardio-vibrational fiducial point in the cardio-vibrational signal of the patient during a systolic phase of a cardiac cycle of the patient's heart. For example, as described above, in one implementation, the processor 104 is configured to measure, during patient activity, at least one time interval (e.g., T1$a$, T1$b$, T1$c$, T1$d$, or T1$e$) between an ECG fiducial point and a cardio-vibrational fiducial point (e.g., an S1 cardio-vibrational biomarker) during one or more cardiac cycles (e.g., ECG signals 200) of the patient's heart.

The processor 104 is then configured to retrieve 625 a standard time interval or a standard time interval range from a data storage 105 or memory on the device 100 or from a database at a remote server location (e.g., server 185 of the exemplary system 10 of FIG. 1). The processor 104 is configured to compare 630 the at least one time interval to the retrieved standard time interval or standard time interval range and provide 635 an output based on the comparison. As will be described subsequently with regard to FIGS. 14A-C, in some implementations, the processor 104 configures the device 100 to display 640 the output on the user interface 108 and/or communicates with a patient device (e.g., a smart phone, smart watch, or other computing device) in communication with the wearable device 100 to display the output.

In implementations, the standard time interval comprises a value from about 80 ms to about 150 ms. For example the standard time interval can comprise at least one of 80 ms, 90 ms, 100 ms, 105 ms, 110 ms, 115 ms, 120 ms, 125 ms, 130 ms, 135 ms, 140 ms, 145 ms and 150 ms. In implementations, the standard time interval can comprise a value selected from a range of about 100 ms to about 140 ms, and in other implementations, the standard time interval can be a value selected from a range of about 110 ms to about 130 ms.

In implementations, the standard time interval range comprises a range of about 80 ms to 150 ms. In implementations, the standard time interval range comprises a range of about 100 ms to 140 ms, and in other implementations, the standard time interval range comprises a range from about 110 ms to 130 ms. For example, the standard time interval range comprises at least one of 80 ms-85 ms, 85 ms-90 ms, 90 ms-95 ms, 95 ms-100 ms, 100 ms-105 ms, 105 ms-110 ms, 110 ms-115 ms, and 115 ms-120 ms, 120 ms-125 ms, 125 ms-130 ms, 130 ms-135 ms, 135 ms-140 ms, 140 ms-145 ms, and 145 ms-150 ms. In other implementations, the standard time interval range can be a range that spans at least one of at least 10 ms, at least 15 ms, at least 20 ms, at least 30 ms, at least 40 ms, at least 50 ms, at least 60 ms and at least 70 ms within the standard time interval range of about 80 ms to about 150 ms.

In implementations, the processor 104 is configured to provide the output based on the comparison when the at least one time interval falls outside of a range, either by falling outside the standard time interval range or by exceeding a certain percentage of the standard time interval range value, for example by exceeding at least one of one percent of the standard time interval, two percent of the standard time interval, five percent of the standard time interval, ten percent of the standard time interval, fifteen percent of the standard time interval, and twenty percent of the standard time interval.

In some implementations, the device 100 provides sensor data to the remote server 185. A processor of the remote server retrieves 645 the standard time interval or the standard time interval range and compares 650 the at least one time interval to the standard time interval or the standard time interval range, and generates 655 a report. The server 185 then provides 660 the report to a physician, other caregiver, patient service representative, or other interested party in communication with the remote server via a caregiver terminal 180, for example. The reports can be provided automatically upon generation or upon request by the end user. In another implementation, the remote server 185 receives the output provided by network interface 106 of the device 100 and generates 655 a report based on the received output from the device 100. Example reports will be described subsequently with regard to FIG. 15. In some implementations, the processor 104 of the device or a processor of the remote server 185 is configured to identify an improving or worsening heart failure condition of the patient based on the output. Additionally or alternatively, the output displayed on the user device 100 or provided in a report enables a patient, physician, other caregiver, or other user to evaluate the monitored physiological data of the patient 175 and identify an improving or worsening condition.

In addition or alternatively, the processor 104 (or a processor of the server 185 receiving monitored data sent from the network interface 106) can be configured to compare the at least one time interval with a prior or subsequently measured time interval corresponding to a prior or subsequent patient activity. In implementations, the processor 104 can be configured to compare the at least one time interval with a prior time interval representing a prior patient activity. Additionally or alternatively, the processor 104 can be configured to compare the at least one time interval with a subsequent time interval representing a subsequent patient activity. The processor 104 of the device 100 or the server 185 is configured to provide an output based on these comparisons and determine an improving or worsening heart failure condition of the patient 175 based on the output. The device 100 and/or server 185 monitors for a worsening condition of the patient and can provide reports and outputs, including audible, visible, and/or tactile alerts to the patient or caregiver in the event of a worsening condition that requires immediate attention.

Figure 7:
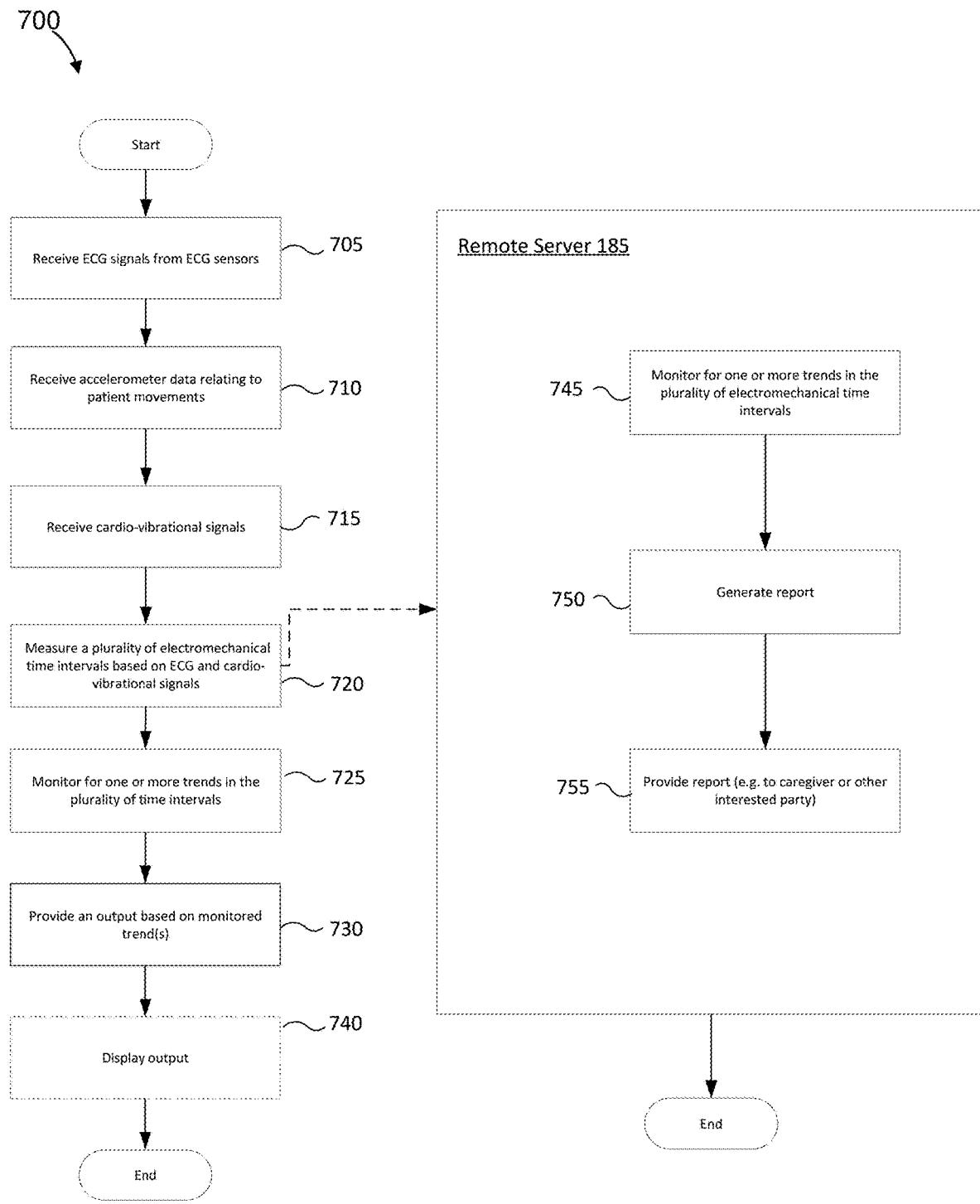
FIG. 7 depicts example methods for identifying physiological conditions.

As shown in FIG. 7 implementations include example methods 700 for evaluating trends in electromechanical time intervals of a patient's heart during patient activity.

The method includes receiving 705 an ECG signal from a one or more of ECG sensors 114 in contact with a torso of a patient 175, receiving 710 information relating to patient movements from an accelerometer 118 disposed on the patient, and receiving 715 a cardio-vibrational signal of the patient 175 from a vibrational sensor 110 disposed on the patient 175. In implementations, the sensors are provided by a wearable cardiac monitoring device 100 as described in implementations described herein throughout. At least one processor 104 of the device 100 measures 720 a plurality of time intervals (e.g., T1$a$, T1$b$, T1$c$, T1$d$, and T1$e$) between an ECG fiducial point on the ECG signal 200 (FIG. 2) and a cardio-vibrational fiducial point in the cardio-vibrational signal 300 (FIGS. 2 and 3) of the patient 175. In implementations, the plurality of time intervals (e.g., T1$a$, T1$b$, T1$c$, T1$d$, and T1$e$) are indicative of systolic function of the patient's heart, and the method 700 of evaluating trends, therefore, is a method of evaluating systolic function of a patient's heart during patient activity.

In implementations, the processor 104 monitors 725 the plurality of measured time intervals for one or more trends indicative of an improving or worsening heart failure condition of the patient 175. As will be described subsequently with regard to FIGS. 14A-C, in some implementations, the processor 104 is configured to provide 730 an output based on the comparison or monitored one or more trends, and, in some implementations, the processor is configured to cause a user interface of the wearable cardiac monitoring device to display 740 an indication of improving or worsening heart failure.

In implementations, the sensor signals are provided to a remote server 185 in communication with the at least one processor 104 via a network interface 106, and the remote server 185 monitors 745 the plurality of measured time intervals for one or more trends indicative of an improving or worsening heart failure condition of the patient 175. In implementations, the remote server 185 generates 750 a report based on the comparison or the one or more monitored trends. In some implementations the remote server 185 provides 755 the report to a caregiver or other party interested in patient management or care. The reports can be provided automatically upon generation and/or in response to a scheduled or unscheduled request by the end user (e.g. the requesting patient, physician, other caregiver, patient care representative, or other authorized user).

In another implementation, the remote server 185 receives the output provided by network interface 106 of the device 100. The server 185 generates a report and provides the report to a physician, other caregiver, patient service representative, or other interested party based on the received output. Example reports will be described subsequently with regard to FIGS. 14A-C and 15. In some implementations, the processor 104 of the device or a processor of the remote server 185 is configured to identify an improving or worsening heart failure condition of the patient based on the output. Additionally or alternatively, the output displayed on the user device 100 or provided in a report enables a patient, physician, other caregiver, or other user to evaluate the monitored physiological data of the patient 175 and identify an improving or worsening condition.

Figure 8:
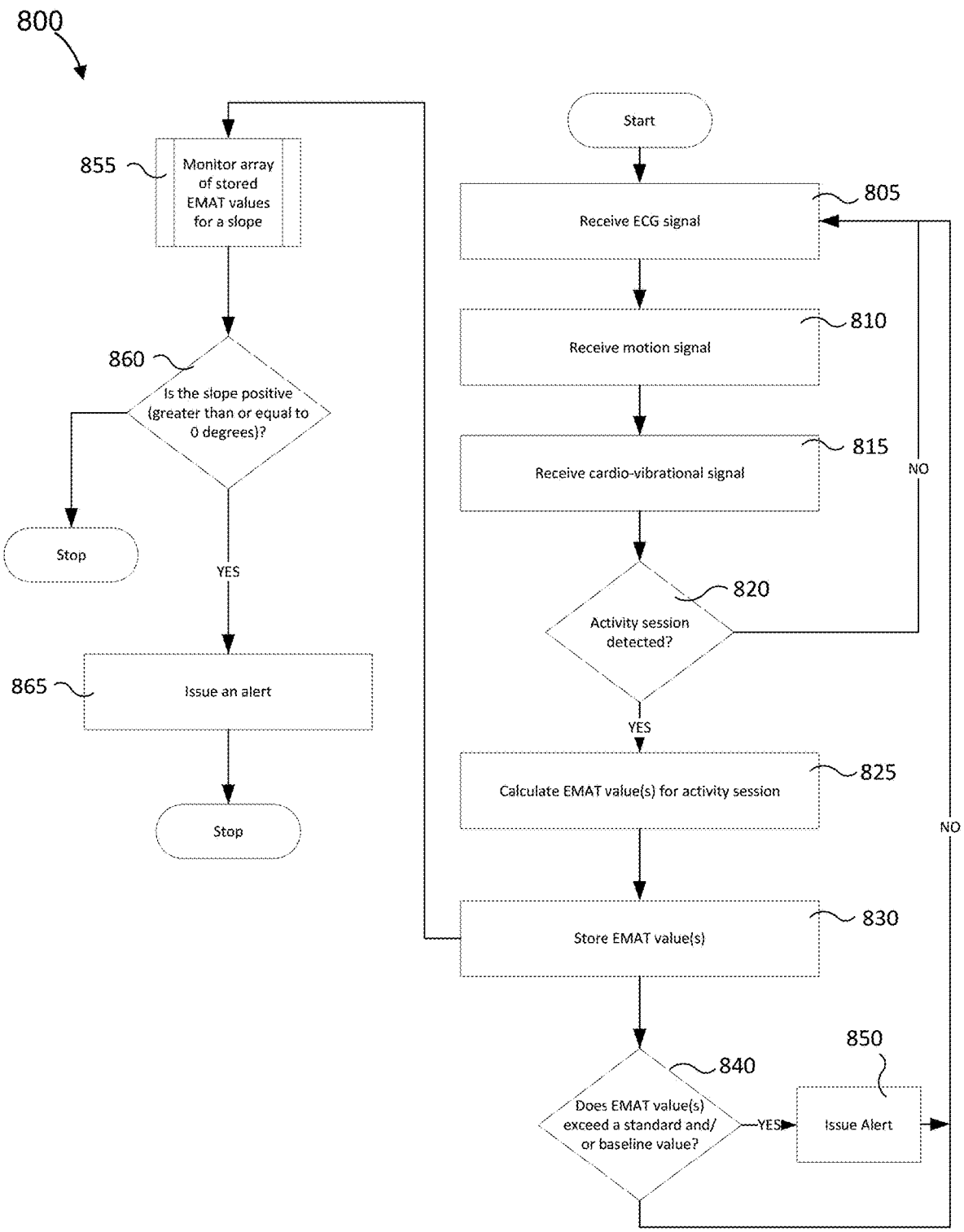
FIG. 8 depicts sample algorithms for monitoring and identifying physiological conditions.

As shown in the example of FIG. 8, in implementations, the processor 104 of the device and/or a processor of the remote server 185 or caregiver terminal 180 perform one or more processing steps for monitoring 800 trends in patient physiological data. Although the monitoring 800 routines of FIG. 8 are described with regard to execution by the processor 104 of the device 100, one or more executable steps can be performed by a remote processor (e.g., a processor of the remote server 185 or remote caregiver terminal 180 of FIG. 1) in communication with the device 100 via a communication network (e.g., communication network 190 of the system 10 of FIG. 1). In implementations, the processor 104 receives 805 an ECG signal, receives 810 a motion signal, and receives 815 a cardio-vibrational signal.

The processor 104 queries whether an activity session is detected. In implementations that will be further described with reference to FIGS. 11A-B and 12A-E, the method includes prompting the patient to engage in the patient activity. In implementations, the patient 175 affirmatively accepts the prompt to engage in activity by pressing a button on the device or a soft button (e.g., a touch screen icon) on the user interface 108 of the device 100 or on the user interface of another computing device (e.g., a smart phone, smart watch, or computer) in wireless communication with the device 100. Upon commencement of the commanded activity and/or acceptance of the commanded activity, the processor stores an activity marker in the signal data that chronologically marks the start of data collected during the patient activity.

In other implementations the method 800 includes automatically detecting the patient is engaged in the patient activity. For example, the processor 104 can determine that the patient is engaged in the patient activity based on detecting a predetermined elevation in a heart rate derived from the ECG signal of the patient, and can store an activity start marker in a memory of the device 100 upon determining that the patient is engaged in the patient activity. As will be described with reference to FIGS. 12A-E and 13A-E, in some implementations, the processor prompts the patient to confirm that the patient is engaged in activity prior to storing the activity start maker in memory.

In some implementations, the predetermined elevation in heart rate that triggers automatic detection of patient activity is an elevation of at least between 5-20% of a baseline or standard heart rate of the patient. For example, the baseline heart rate can be calculated as an average, median, or mode heart rate value of a patient's heart rate over a period of time.

For example, a standard heart rate can include a predefined value that is determined at design time and/or stored as a user-defined value in a memory of the device or retrieved from a remote server. For example, the standard heart rate values can be determined based on patient's characteristics such as an age, medical history, previous fitness history, and/or other factors.

Alternatively or additionally, the processor 104 may determine the patient is engaged in a patient activity when the predetermined elevation of heart rate is over a duration of at least between 1 to 5 minutes. In addition to or alternatively to monitoring ECG signals, the processor 104 may determine the patient is engaged in the patient activity based on signals from a motion sensors, such as the accelerometer 118 of the device 100 of FIG. 1. In some implementations, the processor 104 identifies motion based on the motion sensor data and subsequently monitors the ECG signal of the patient to verify an elevation in heart rate.

Once the processor 104 determines 820 that an activity session is detected, the processor 104 calculates 825 an electromechanical time interval, such as an EMAT value, for the activity session. In implementations, the EMAT value can be a representative value for all measured EMAT time intervals recorded during a patient activity. The EMAT value can be calculated, for example, based averaging on a plurality of EMAT values, taking a median value, a mode value, and/or smoothing the values by ignoring outliers during the patient activity. In some examples, each of the plurality of EMAT values represents a single cardiac cycle (e.g., ECG signal 200) during the patient activity. In other examples, each EMAT value of the plurality of EMAT values is first calculated as a single representative value for a selected number of cardiac cycles 200, e.g., 10 cardiac cycles during the patient activity. In such an implementation, each of the plurality of EMAT values recorded during an activity represents the average, median, mode, or other representative value for an interval of 10 cardiac cycles, or heart beats during the patient activity. In some examples, the EMAT value for a patient activity can be selected at random from values measured during a certain portion of the patient activity, such as the middle third or last half of the duration of the patient activity, when heart rate has been elevated continuously for a period of time (e.g., between at least 2-5 minutes, at least 5-10 minutes, at least 10-15 minutes, or other user-configurable or predefined period of time) ensuring reliable correlation of heart rate elevation to electromechanical time interval data.

Once the processor calculates one or more EMAT values for a patient activity, the processor stores 830 the EMAT value(s) in a data storage 105 on the device or in a remote database, in communication with the device via a communication network. The processor 104 determines 840 whether the EMAT value(s) exceed a standard and/or baseline value, and if the EMAT value(s) exceed a standard and/or baseline value, the processor 104 issues 850 an alert to the patient and/or caregiver while continuing to monitor signals from one or more physiological sensors. If the EMAT value(s) do not exceed a standard and/or baseline value, the processor 104 continues monitoring signals from one or more physiological sensors and calculating EMAT values for one or more instances of patient activities. For example, the processor 104 may employ the methods of FIGS. 4 and 6, to compare the current EMAT values to baseline and/or standard values.

Further, in some implementations, a physician, other caregiver, patient service representative, or other authorized person can customize an EMAT threshold parameter at which the processor 104 will issue an alert for a calculated EMAT value. For instance, a device 100 and/or remote server 185 can be configured to store a predetermined standard EMAT value or range (as described in detail above) as a default value or range for the EMAT alert threshold parameter. An authorized person can change the parameter by modifying the stored value. Standard EMAT time intervals and time interval ranges change with diagnoses and age because heart muscle stiffens with age and underlying heart diseases. In implementations, standard time intervals and ranges can be selected based on patient condition (e.g., hypertension, diabetes, coronary artery disease, non-ischemic cardiomyopathy), severity of condition, length of disease state, age, gender, and/or other medical conditions. Accordingly, as a patient's health changes, a physician or caregiver may elect to change the EMAT threshold parameter values against which monitored EMAT values are compared.

Over an extended period of time (e.g., over a period of 1-4 weeks, 4-6 weeks, 1-3 months or more), the processor 104 may store an array of EMAT values corresponding to a plurality of patient activities performed over the extended period. In some implementations, the processor 104 can cause each of the EMAT values to be transmitted to a remote server for storage and analysis substantially immediately after each EMAT value is determined.

Figures 9A, 9B:
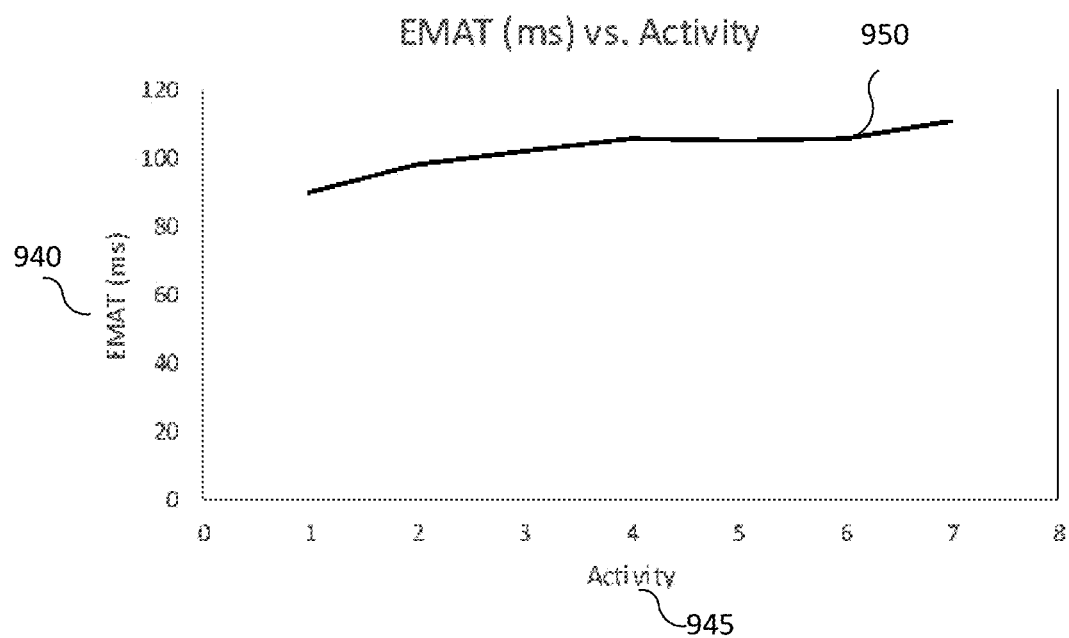
FIGS. 9A and 9B depict example outputs of physiological data collected during patient activity.

The processor 104 can implement a processing routine to monitor and analyze the array of stored EMAT values. Alternatively or additionally, a remote server can be configured to perform the processing routine for monitoring and analyzing the array of stored EMAT values. For example, as depicted in FIG. 9A, an array of EMAT values 940 and average heart rates 935 are recorded and monitored 855 for a number of sessions 945 of patient activity (e.g., Activity 1 through Activity 7). These can be activities performed on one or more days, weeks, or months during a period of wear of the cardiac monitoring device 100. As depicted in FIG. 9B, the processor 104 (and/or a remote server) monitors the slope of the trend line 950 of EMAT values and determines 860 whether the slope of the trend is greater than or equal to zero. If the slope is decreasing, the processor 104 (and/or remote server) determines that the heart failure condition is improving. If the slope is increasing or remaining constant, the processor 104 (and/or remote server) issues an alert 865 indicating a continued or worsening heart failure condition.

In some examples, the processor 104 can be configured to monitor, during the patient activity, other types of cardiovibrational information apart from electromechanical time intervals and analyze the information. For example, such cardio-vibration information can include LVST and S3 strength data. As in the case of analysis of electromechanical time intervals described previously with regard to the examples of FIGS. 4 through 9B, the analysis can involve baseline analysis, standards analysis, and/or trends analysis.

In addition to or alternatively to monitoring one or both of EMAT trends and cardo-vibrational time interval trends, in implementations, the processor can be configured to monitor cardio-vibrational strength of a cardio-vibrational biomarker (e.g., S1, S2, S3, and S4). For example, the processor 104 can be configured to measure, during a patient activity, an S3 cardio-vibrational biomarker strength derived from the cardio-vibrational signal 300.

Figure 10:
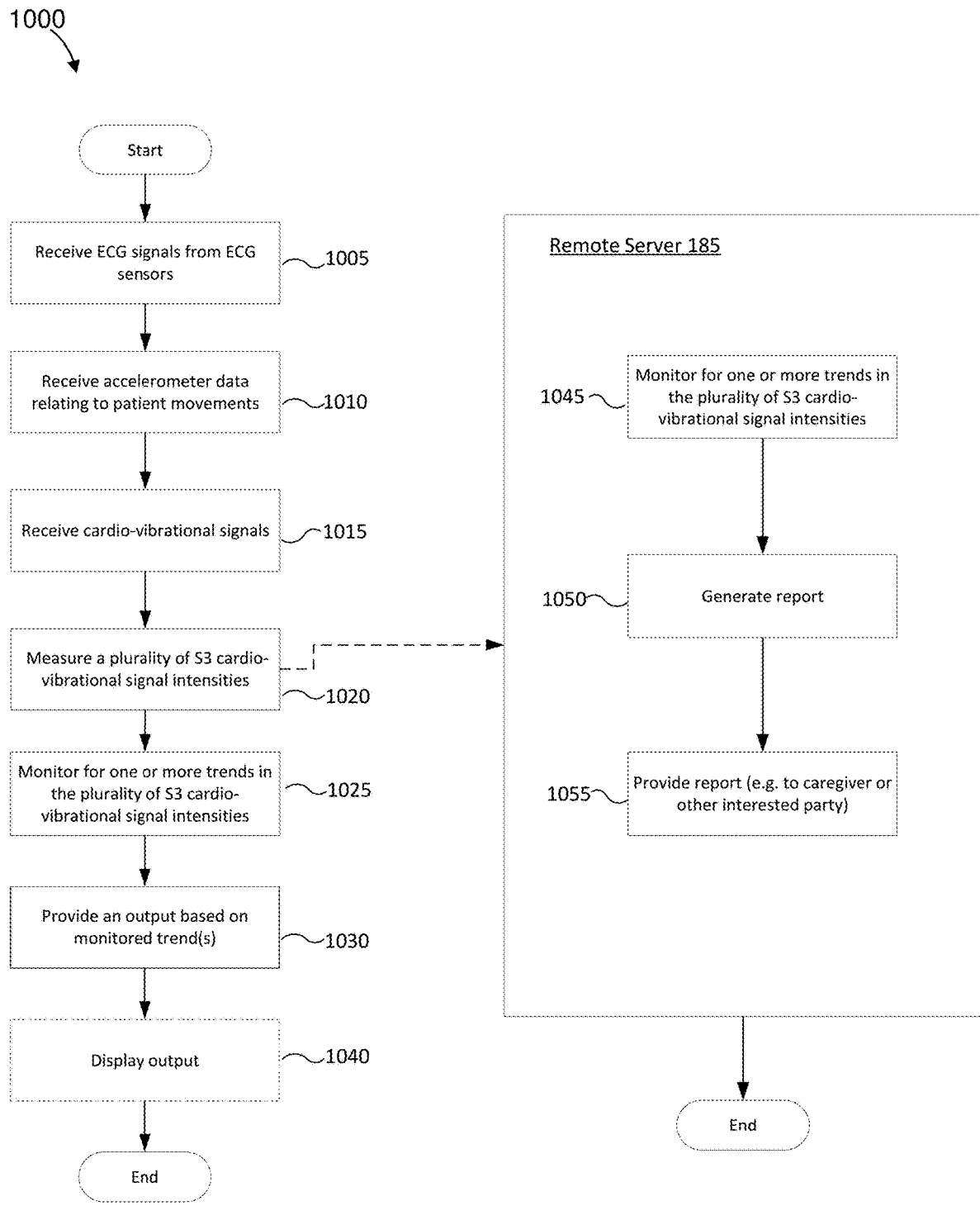
FIG. 10 depicts example methods for identifying physiological conditions.

As shown in the example monitoring method 1000 of FIG. 10, the processor 104 receives 1005 an ECG signal from one or more ECG sensors 114 in contact with a torso of a patient 175, receives 1010 information relating to patient movements from an accelerometer 118 disposed on the patient, and receives 1015 a cardio-vibrational signal of the patient 175 from a vibrational sensor 110 disposed on the patient 175. In implementations, the sensors are provided by a wearable cardiac monitoring device 100 as described in implementations described herein throughout. At least one processor 104 of the device 100 measures 1020 a plurality of S3 cardio-vibrational biomarker strengths in the cardio-vibrational signal. The S3 strengths can each be associated with a distinct interval of physical activity and stored in an array in the data storage 105 of the device 100 or transmitted to the remote server 185. Over an extended period of time (e.g., over a period of 1 to 4 weeks, 4 to 6 weeks, 1 to 3 months or more), the processor 104 may store an array of S3 strength values corresponding to a plurality of patient activities performed over the period. For example, the processor 104 can cause each of the S3 strength values to be transmitted to a remote server 185 for storage and analysis substantially immediately after each S3 strength value is determined.

In implementations, the processor 104 monitors 1025 the plurality of S3 cardio-vibrational biomarker strengths stored in the array for one or more trends indicative of an improving or worsening heart failure condition of the patient 175. As will be described subsequently with regard to FIG. 15, in some implementations, the processor 104 is configured to provide 1030 an output based on the comparison or monitored one or more trends, and, in some implementations, the processor is configured to cause a user interface 108 of the wearable cardiac monitoring device 100 to display 1040 an indication of improving or worsening heart failure.

In implementations, the sensor signals are provided to a remote server 185 in communication with the at least one processor 104 via a network interface 106, and the remote server 185 monitors 1045 the plurality of measured S3 cardio-vibrational biomarker strengths for one or more trends indicative of an improving or worsening heart failure condition of the patient 175. In implementations, the remote server 185 generates 1050 a report based on the comparison or the one or more monitored trends. In some implementations the remote server 185 provides 1055 the report to a caregiver or other party interested in patient management or care. The reports can be provided automatically upon generation or upon request by the end user (e.g. the requesting physician, other caregiver, patient, or patient care representative).

In another implementation, the remote server 185 receives the output provided by network interface 106 of the device 100. The server 185 generates a report and provides the report to a physician, other caregiver, patient service representative, or other interested party based on the received output. Example reports will be described subsequently with regard to FIG. 15. In some implementations, the processor 104 of the device or a processor of the remote server 185 is configured to identify an improving or worsening heart failure condition of the patient based on the output. Additionally or alternatively, the output displayed on the user device 100 or provided in a report enables a patient, physician, other caregiver, patient care representative or other authorized user to evaluate the monitored physiological data of the patient 175 and identify an improving or worsening condition.

In a similar manner, processor 104 can be configured to monitor, during the physical activities, cardio-vibrational time interval values T3 (FIGS. 2 and 3) measured from a first cardio-vibrational fiducial point 305 of an S1 cardio-biomarker biomarker to a second cardio vibrational fiducial point 310 on an S2 cardio-vibrational biomarker for each cardiac cycle (e.g., ECG signal 200). In some implementations, the measured cardio-vibrational time interval values are LVST interval values. In such cases, the processor 104 can implement a process similar to example monitoring method 1000 where LVST interval values are monitored, stored, and analyzed in addition or as an alternative to the S3 strength values. In any of the preceding examples, the processor 104 can be included in a wearable device, such as the wearable cardiac device 100 of FIG. 1. In some examples, the device 100 comprises a garment configured to be worn about the torso and the garment supports one or more ECG sensors 114. In some implementations, the device 100 is a treatment device, such as a wearable defibrillator, and includes at least two therapy electrodes configured to deliver energy to the torso of the patient. The device 100 can be worn for a prescribed period of wear of at least between one day and one week, one week and two weeks, two weeks and one month, one moth and two months, one month and three months, three months and six months, and six months and one year. In some implementations, the device 100 includes a vibrational sensor 110 that includes an accelerometer.

Figure 11A:
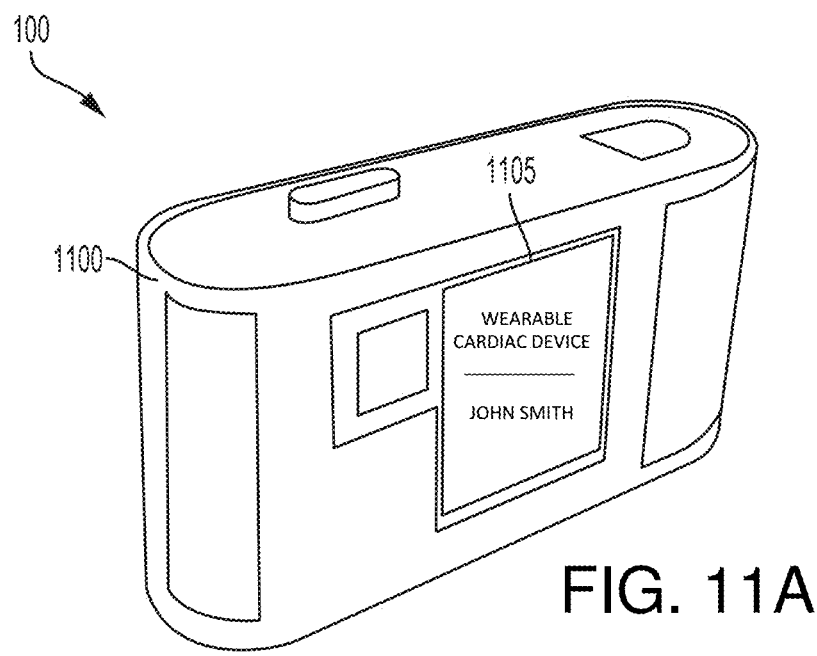
FIGS. 11A-B depict example user interfaces of a patient-worn medical device.
Figure 11B:
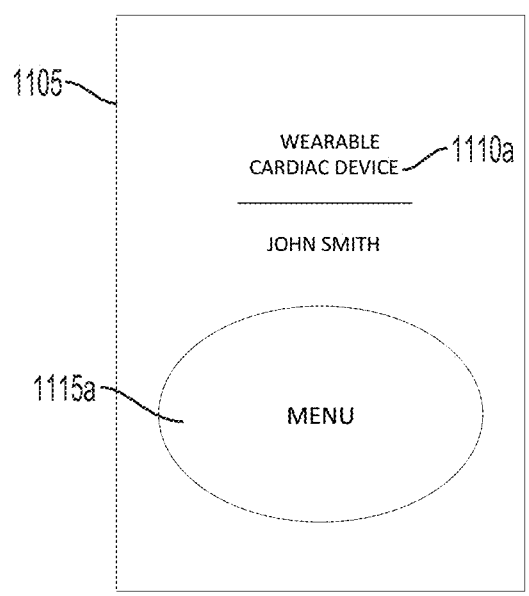

As depicted in FIGS. 11A and 11B, in implementations, the device 100 may include a controller 1100 and a user interface including a display screen 1105. The display screen 1105 may include visible indicia 1110a and one or more selectable buttons or capacitive touch fields 1115a.

As described above with regard to FIG. 8, for example, in implementations, the device 100 can prompt the patient to engage in a patient activity. In examples of a display screen 1105 of a device 100, a patient is prompted with at least one of audible, visible, and tactile alerts to being a patient activity. For example, as shown in FIGS. 12A-12E, a series of screen prompts guide a patient through a process of initiating and completing an activity. In on example, the display screen 1105 can be a user interface that includes written indicia 1110b requesting a patient initiate an activity. As shown in FIG. 12A, the display screen 1105 may include an icon 1120a for assisting the patient in readily associating the request with performing an activity. The display screen 1105 also may include one or more selectable buttons 1115b-c for acknowledging the request or requesting additional information. Once a patient touches or presses the acknowledgement button 1115b, in some implementations, as shown in FIGS. 12B-C, the display screen 1105 may present a selectable option for initiating activity immediately or delaying until a later time (1110c). The patient may select an option for starting the activity immediately by, for example, touching a touch field 1115d indicating immediately starting the activity. Alternatively, the patient may select a later start time by touching a touch field 1115e indicating intent to engage in the activity at a later time.

As shown in FIG. 12D, the device 100 then prompts the patient to begin the activity with one or more of written indicia 1110d and icons 1120b. The device 100 may further include audible instructions and/or alert sounds prompting the patient to acknowledge the start of activity. In some examples, the patient affirmatively starts the patient activity by indicating to the device that activity is commencing. The patient may do this by verbally acknowledging the prompt to begin activity, and/or by pressing a button or touching a touch field 1115b on the user interface display screen 1105. As will be described with regard to FIGS. 13A-E, in some implementations, the device 100 automatically detects the start of a patient activity and asks the patient to confirm the start of the activity.

In some implementations, the patient activity is a prescribed activity prompted by the device 100 at scheduled intervals. In some implementations, the device 100 includes a network interface 106 configured to communicate with a remote server 185, as described in the example system 10 of FIG. 1. The remote server 185 can be configured to transmit an instruction to the device 100 via the network interface 106 to prompt the patient 175 to initiate the patient activity. In some implementations, the instruction may initiate from a caregiver terminal 180 in communication with the remote server 185 via the communication network 190. In this way, a physician or other caregiver can request that the patient 175 perform an activity during which the device 100 will collect physiological data for analysis and subsequent development of a patient treatment regimen.

In some implementations, the patient activity comprises a predetermined activity duration of between at least 3 to 6 minutes, between at least 6 to 12 minutes, between at least 12 to 15 minutes, between at least 15 to 20 minutes, between at least 20 to 30 minutes, between at least 30 to 45 minutes, and between at least 45 minutes to an hour. By engaging the patient 175 in a sustained patient activity, the device 100 ensures the patient will achieve an elevated heart rate. This ensures monitoring of relational trends and changes in physiological factors indicative of heart condition, such as cardio-vibrational biomarker presence and strength, and electromechanical time intervals. At the completion of the patient activity, as shown in FIG. 12E, the display screen 1105 requests that the patient stop activity (1110e) and provides input buttons or touch fields 1115b, 1115c for acknowledging the end of the patient activity. By requesting that the patient affirmatively acknowledge the start and stop of a patient activity, the processor 104 of the device 100 is able to store a marker in the recorded physiological data (e.g., ECG signal, cardio-vibrational signal, accelerometer data) that identifies the data as having been collected during a patient activity.

As indicated previously, in some examples, the device 100 automatically detects that the patient has engaged in a patient activity and requests confirmation to store a marker in the data collected by one or more physiological sensors. For example, FIGS. 13A-E depict display screens 1105 indicating that the device has detected an activity (1110f) and requesting that the patient select (1110g) either a touch field 1115f confirming engagement in an activity or touch field 1115g denying engagement in an activity (1110h, 1110i). If the patient confirms engagement in an activity, the device 100 monitors the one or more sensors identifying the activity, such as an accelerometer 1118 detecting movement of the patient, until activity ceases. When the device 100 detects the termination of the activity, a display screen 1105 prompts the patient to confirm completion of the activity (1110j, 1110l), e.g., by selecting either a touch field 1115f confirming cessation of the activity or touch field 1115g indicating continuation of the activity (1110k). Similarly to the previous example, the processor 104 of the device 100 stores a marker in the collected and recorded data to indicate the affirmatively acknowledged start and stop of the patient activity.

As described previously with regard to the examples of FIGS. 4, 6, 7, and 10, the processor 104 is configured to provide output based on the physiological data collected by various sensors, such as one or more of the at least one ECG sensor 114, the vibrational sensor 110, and the accelerometer 118 of the example device 100 of FIG. 1. In some examples, the output can be provided on a user interface of the device 100, such as a display screen 1105 (FIG. 11), and, alternatively or additionally, the output can be provided in a report to a physician, other caregiver, or other interested recipient.

FIGS. 14A-C provide examples of output presented on a display screen 1105 of the device 100. In some examples shown in FIGS. 14A-B, the display screen 1105 provides written indicia indicating monitored physiological data and baseline or standard data 1110m, 1110n. A patient is able to compare their current measured and/or calculated results against these baseline and/or standard values. The patient can confirm receipt of the output by engaging a button or touch field 1115b of the display screen 1105. In another example shown in FIG. 14C, the display screen 1105 provides (1110p) a plot 1400 showing recorded data and a trend line linking the progression of values. In the example of FIG. 14C, the display screen 1105 includes a plot 1400 showing the monitored trend in EMAT values, and the patient's values have decreased between each of four patient activities sessions executed on each of four days, indicating an improving cardiac condition.

Figure 15:
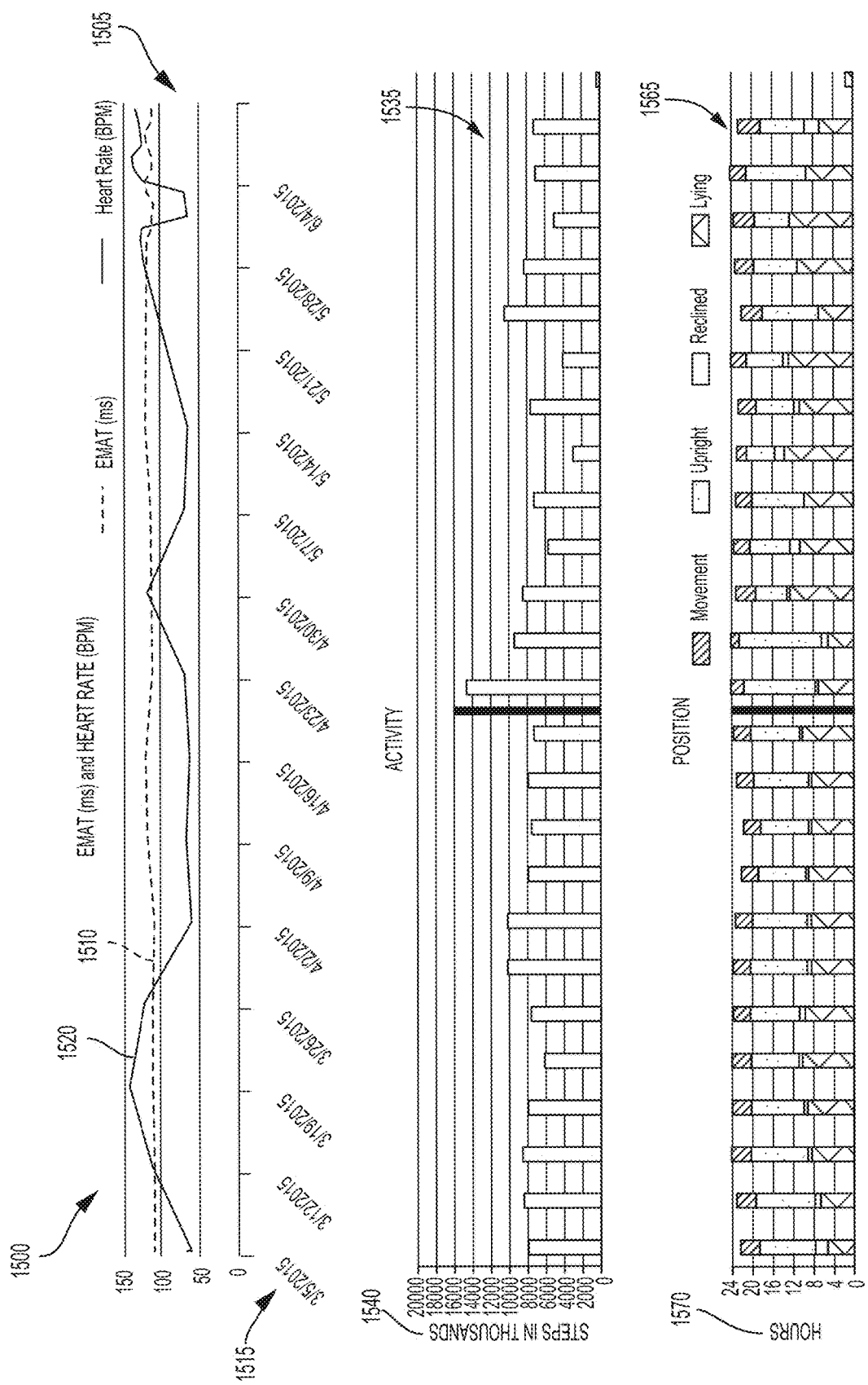
FIG. 15 depicts example reports based on physiological data collected during patient activity.

Similarly, physicians and other caregivers review the data collected by the device 100 to discern whether a patient's cardiac health is improving or worsening. FIG. 15 shows an example report 1500 of data collected by the device 100 and provided to a requesting physician or other caregiver. In some implementations, the example report 1500 is generated by the remote server 185 in communication with the device and the caregiver terminal 180 through the communication network 190. The server 185 can push the report to the caregiver terminal 180 at regular and/or scheduled intervals, and/or the server can generate and provide the report upon request.

The example report 1500 of FIG. 15 provides a plot 1505 of EMAT values 1510 over a number of patient activities on a number of days 1515 and, optionally in some implementations, a concurrent plot of heart rate 1520. In the example of plot 1505, the patient's EMAT values have remained constant across a range of elevated heart rates, indicating that the patient's heart failure condition is not improving and could be worsening.

The report 1500 may include one or more additional plots that assist a physician or other caregiver in determining the status of the patient's cardiac health condition. For example, an activity bar plot 1535 indicates, for the same patient activity sessions presented in the EMAT plot, the number of steps 1540 taken by the patient during the activity. The recipient of this report can draw inferences between the patient's heart rate and how many or few steps contributed to an elevation in heart rate, for example. In another example, the report may include one or more position bar plots 1565 showing, for the same patient activity sessions presented in the EMAT plot, the hours 1570 the patient 175 spent in various positions during the activity. The recipient of this report can draw inferences between the patient's heart rate and how strenuous the activity was for the patient given their body position during a period of heart rate elevation, for example. By providing a physician or caregiver with a snapshot of several monitored and/or calculated descriptors of physiological health, the system 10 provides a more holistic view of the patient's overall health. This can assist with devising an effective treatment plan based on individualized needs and conditions of each patient.

As described previously with regard to the examples of FIGS. 4 through 10, the processor 104 is configured to provide output based on the physiological data collected by various sensors, such as one or more of the at least one ECG sensor 114, the vibrational sensor 110, and the accelerometer 118 of the example device 100 of FIG. 1. In some examples, the output can be provided by a processor 104 of the device or by the server 185 performing a linear or non-linear logistic regression analysis on the physiological data collected by various sensors. In one example, the output of the logistic regression analysis can be a normalized score. In one example, the normalized score considers many factors for each patient. The logistic regression analysis therefore can normalize a collective value within a comparison rating scale of 0 to 1, where the collective value represents a numerical evaluation of a combination of the monitored and derived physiological data. In another example, the normalized score considers many factors for each patient and normalizes the monitored and derived physiological data within a comparison rating scale of 0 to 100. In some examples, the normalized score considers many factors for each patient and normalizes the monitored and derived physiological data within a non-linear comparison rating scale such as a logarithmic or exponential scale.

Figure 16:
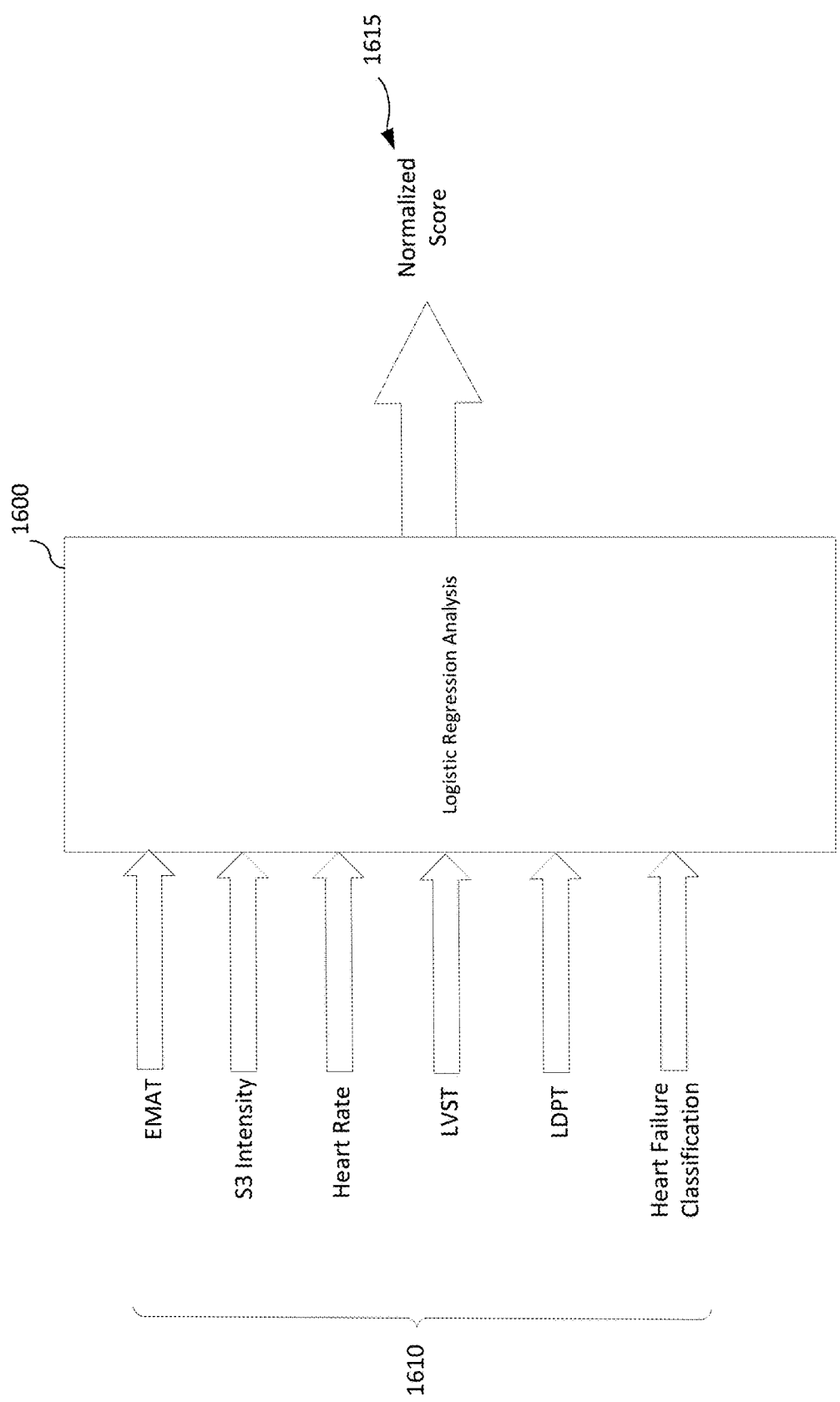
FIG. 16 depicts example physiological response data analysis.

FIG. 16 shows a logistic regression analysis 1600 for use with some of the implementations herein. For example, analysis 1600 can be implemented through encoded instructions stored on a memory and configured to be executed by the processor 104 (or a remote server 185). For example, physiological data 1610 measured and/or derived by device 100 during patient activity can be input to the analysis 1600. The provided data 1610 may include at least an electromechanical time interval value, for example EMAT, and at least one or more of an S3 cardio-vibrational biomarker strength, heart rate, patient demographics, and a heart failure classification for the patient. In some examples patient demographics can include age, gender, patient condition (e.g., hypertension, diabetes, coronary artery disease, non-ischemic cardiomyopathy), severity of condition, length of disease state, and other medical conditions.

In one example, heart failure classification can be the New York Heart Association classification of Classes I through IV that accounts for symptom severity and the amount of exertion required to prompt symptoms. In another example, the heart failure classification can be the American Heart Association classification of Classes I through IV covering severity of a patient's symptoms and Objective Assessment Classes A through D covering a physician's assessment of patient's symptoms. In implementations, the device 100 may automatically classify heart failure into the appropriate classes and/or stages of heart failure. In some implementations physician, other caregiver, or patient care representative can configure in advance which classification scheme the device 100 is to implement. For example, a physician can be prompted at set up to indicate a classification scheme by indicating a selection via a user interface (e.g., either locally, on the device, or via a remote configuration parameter on a server that is then transmitted to the device).

The logistic regression analysis 1600 receives the provided data 1610 and outputs a normalized score 1615. This normalized score 1615 is then available to a physician or other caregiver for evaluating a patient's condition and adjusting treatment according to the value of the normalized score 1615. For example, on a normalized scale of 0 to 1, a score of 0.5 or greater is configured to indicate worsening health. A score of 0 to 0.5 can be configured to indicate improving health. By receiving one or more scores across a period of patient wear of the device 100, a physician, other caregiver, patient service representative, or other authorized user can assess the overall health of the patient using a holistic approach to considering physiological factors.

In implementations, relative weights for each input parameter (e.g., measured and derived physiological data 1610) can be used in the logistic regression analysis 1600 to correlate the relative linear effects of each of the input parameters comprising the input data 1610. In other examples, as mentioned previously, a non-linear regression analysis may also be employed, which may for example involve polynomial or exponential terms. The weighting of the different input parameters in the score permits a system to actually focus on addressing the input parameters (e.g., input data 1610) that will most affect the output score 1615.

In one example, a model for simple linear regression can be:

$$Y = b_0 + b_1 X_1 + b_2 X_2 + b_3 X_3 + \cdots + b_i X_i$$

where Y is the dependent variable, X is the independent variable, and b is the regression parameter (e.g., the intercept and the slope of the line of best fit). The coefficients, $b_i$, for each input parameter, $X_i$, are calculated using statistical methods such as the general linear model to provide a best estimate a score, Y. In some examples, the coefficients, $b_i$, can calculated using measured physiological data collected from a statistically varied population of samples to provide a robust database for accurate model generation.

In other implementations, matrix analysis can be applied to the general linear model for logistic regression analysis, randomized block designs, incomplete block designs, fractional factorial designs, Latin square designs, split plot designs, crossover designs, and nesting. In one example, the model for matrix analysis can be:

$$Y = XB + e$$

where Y is a vector or matrix of dependent variables, X is a vector or matrix of independent variables, B is a vector or matrix of regression coefficients, and e is a vector or matrix of random errors.

In examples including multivariate models, Y can be a matrix of continuous measures. The X matrix can be either continuous or categorical variables, according to the type of model. For some example multivariate models, the system 10 implements analysis of variance (ANOVA) to analyze models with multiple dependent variables and zero (e.g., only the constant is present), one, or more categorical independent variables.

In some examples, regression analysis may also be performed using the following logistic function:

$$Y = 100\left[1 - \frac{1}{\left(1 + e^{b_0 + \Sigma b_i X_i}\right)}\right]$$

In examples, a state transition matrix can be developed using a Markov model. The threshold can be adjusted as well as different weighting coefficients applied based on the Markov model estimation. In some examples, Forward-Backward and Baum-Welch algorithms are performed with measured and derived physiological data 1610 to build a hidden Markov model.

Figure 17:
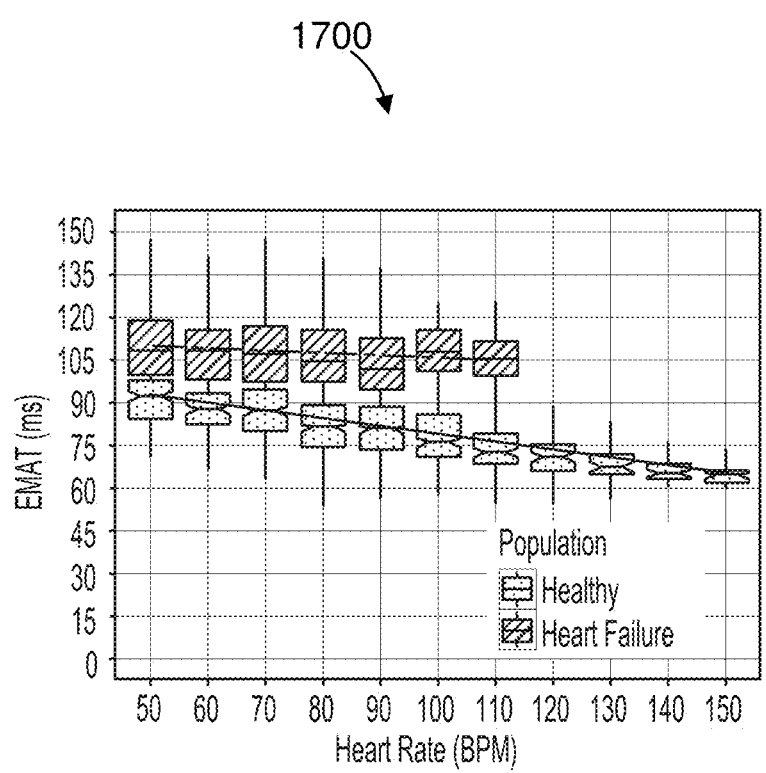
FIG. 17 depicts example physiological response data trends for an electromechanical time interval.

Turning now to FIG. 17, EMAT trends 1700 indicative of worsening or unchanged heart failure include substantially unchanged EMAT values during an activity that increases patient heart rate. In a study, cardio-vibrational and heart rate information was collected from a first group of 15 healthy volunteers (87% male, average age: 33±15 years) during graded exercises. The 15 healthy volunteers each wore a cardio-vibrational cardiography-enabled accelerometer with ECG electrodes. Cardio-vibrational information and heart rate data were also accumulated from a second group of 1433 acute heart failure patients with an ejection fraction (EF) ≤35% (78% male, age: average 58±13 years). The heart failure patients each wore a cardio-vibrational cardiography-enabled wearable cardioverter defibrillator. At least the following systolic and diastolic cardio-vibrational information was calculated from the recorded heart sounds and ECG signals: electromechanical activation time (EMAT), left ventricular systolic time (LVST), and S3 cardio-vibrational biomarker strength (e.g., calculated based on cardio-vibrational intensity and persistence, and expressed on a scale of 0 to 10 units, or strength units).

As shown in FIG. 17, for healthy subjects, the EMAT trend 1700 showed a statistically significant ($p<0.05$) decrease with increased heart rate. For heart failure patients, EMAT did not present a statistically significantly change with increased heart rate. For example, for a heart rate of 90 beats per minute (bpm), EMAT was approximately 105 ms for heart failure patients and 80 ms for healthy patients, a difference of approximately 25 ms. For example, for a heart rate of 100 bpm, EMAT was approximately 110 ms for heart failure patients and 75 ms for healthy patients, a difference of approximately 35 ms. For example, for a heart rate of 110 bpm, EMAT was approximately 107 ms for heart failure patients and 70 ms for healthy patients, a difference of approximately 37 ms. As heart rate increased, the gap between EMAT values for heart failure patients and healthy patients increased because the EMAT values dropped for healthy patients and remained substantially constant for heart failure patients during elevation of the heart rate.

Figure 18:
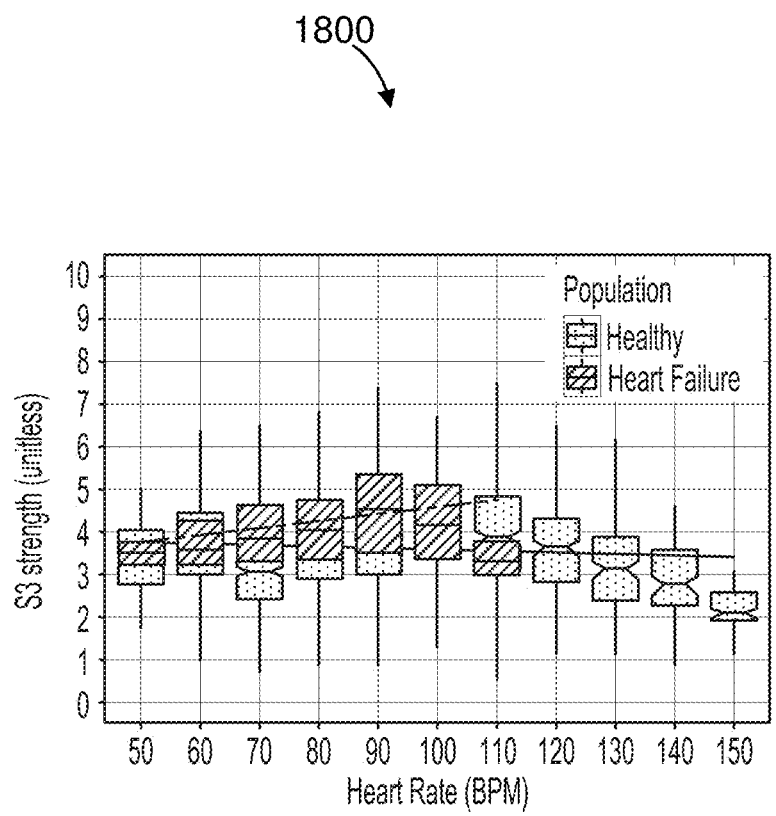
FIG. 18 depicts example physiological response data trends for cardio-vibrational biomarker strength.

As shown in FIG. 18, an S3 strength trend 1800 showed no change in S3 strength with heart rate in healthy subjects, but showed a statistically significant increase with increased heart rate in the heart failure group.

During activity, the release of catecholamines increases heart rate and stroke volume. In a healthy heart, electromechanical time intervals of a cardiac cycle, such as those of FIG. 2, present at particular time intervals relative to certain cardio-vibrational biomarkers in a cardio-vibrational signal 300. These time intervals vary as heart rate increases. In an unhealthy heart, the same underlying catecholamines result in increased heart rate. Although the underlying mechanics are comparable for healthy and unhealthy hearts, the electromechanical time intervals of an unhealthy heart differ from those of a healthy heart. Monitoring these time intervals of unhealthy hearts relative to healthy hearts can provide information on worsening systolic and diastolic cardiac conditions as heart rate increases.

In contrast to healthy subjects, EMAT did not change with heart rate in the heart failure group, implying an inability to increase contractility with demand. S3 strength showed an increase with heart rate in the heart failure group suggesting reduced ventricular compliance in early diastole. EMAT and S3 could be used independent of, or in conjunction with, heart rate for ambulatory monitoring of heart failure and for providing a useful signal by which to guide therapy. By monitoring heart rate, electromechanical time intervals, and the presence of cardio-vibrational biomarkers, the device 100 enables monitoring, and subsequent analysis and treatment of cardiac conditions.

The teachings of the present disclosure can be generally applied to extracting physiological information from external medical monitoring and/or treatment devices (e.g., devices that are not completely implanted within the patient's body) for further processing. External medical devices for extracting physiological data in accordance with implementations of the present disclosure can include, for example, ambulatory medical devices that are capable of and designed for moving with the patient as the patient goes about his or her daily routine. An example ambulatory medical device for use with any of the preceding examples can be a wearable medical device (e.g., the device 100) such as a wearable cardioverter defibrillator (WCD), a wearable cardiac monitoring device, an in-hospital device such as an in-hospital wearable defibrillator (HWD), a short-term wearable cardiac monitoring and/or therapeutic device, mobile cardiac monitoring devices, and other similar wearable medical devices.

A wearable medical cardiac-monitoring device is capable of continuous use by the patient. Such continuous use can be substantially or nearly continuous in nature. During substantially continuous or nearly continuous use, the wearable medical device can be continuously used except for sporadic periods during which the use temporarily ceases (e.g., while the patient bathes, while the patient is refit with a new and/or a different garment, while the battery is charged/changed, while the garment is laundered, etc.). Such substantially continuous or nearly continuous use as described herein may nonetheless qualify as continuous use. In some implementations, the patient may remove the wearable medical device for a short portion of the day (e.g., for half an hour while bathing).

Further, the wearable medical device can be configured as a long term or extended use medical device. Such devices can be designed to be used by the patient for a long period of time, for example, a period of 24 hours or more, several days, weeks, months, or even years. Accordingly, the long period of use can be uninterrupted until a physician or other caregiver provides specific prescription to the patient to stop use of the wearable medical device. For example, the wearable medical device can be prescribed for use by a patient for a period of at least one week. In an example, the wearable medical device can be prescribed for use by a patient for a period of at least 30 days. In an example, the wearable medical device can be prescribed for use by a patient for a period of at least one month. In an example, the wearable medical device can be prescribed for use by a patient for a period of at least two months. In an example, the wearable medical device can be prescribed for use by a patient for a period of at least three months. In an example, the wearable medical device can be prescribed for use by a patient for a period of at least six months. In an example, the wearable medical device can be prescribed for use by a patient for a long period of at least one year.

Regardless of the period of wear, the use of the wearable medical device can include continuous or nearly continuous wear by the patient as previously described. For example, the continuous use can include continuous wear or attachment of the wearable medical device to the patient. In implementations, the continuous attachment is through one or more of the electrodes as described herein during both periods of monitoring and periods when the device may not be monitoring the patient but is otherwise still worn by or otherwise attached to the patient. Continuous use can include continuously monitoring the patient while the patient is wearing the device for cardiac-related information (e.g., electrocardiogram (ECG) information, including arrhythmia information, cardiac vibrations, etc.) and/or non-cardiac information (e.g., blood oxygen, the patient's temperature, glucose levels, tissue fluid levels, and/or pulmonary vibrations). For example, the wearable medical device can carry out its continuous monitoring and/or recording in periodic or aperiodic time intervals or times (e.g., every few minutes, hours, once a day, once a week, or other interval set by a technician or prescribed by a caregiver). Alternatively or additionally, the monitoring and/or recording during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device can be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the previously-described in-hospital defibrillator described.

In some implementations, the medical device can be a patient monitoring device with no treatment or therapy functions. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's ECG information, heart rate information, cardio-vibrations (e.g., using accelerometers or microphones), and other related cardiac information. A cardiac monitoring device is a portable device that the patient can carry around as he or she goes about a daily routine. The cardiac monitoring device can be implemented in a garment worn about the torso of the patient or implemented in an adhesively coupled device attaching directly to the torso of the patient. The cardiac monitor can be configured to detect the patient's ECG through a plurality of cardiac sensing electrodes. For example, a cardiac monitor can be attached to a patient via at least three adhesive cardiac sensing electrodes disposed about the patient's torso. Such cardiac monitors are used in cardiac event monitoring, e.g., in patient populations reporting irregular cardiac symptoms and/or conditions. Example cardiac conditions can include atrial fibrillation, bradycardia, tachycardia, atrioventricular block, Lown-Ganong-Levine syndrome, atrial flutter, sino-atrial node dysfunction, cerebral ischemia, syncope, atrial pause, and/or heart palpitations. For example, such patients can be prescribed a cardiac monitor for an long period of time, e.g., 10 to 30 days, or more.

In some mobile cardiac event monitoring applications, a portable cardiac monitor can be configured to substantially continuously monitor the patient for a cardiac anomaly, and when such an anomaly is detected, the monitor may automatically send data relating to the anomaly to a remote server. The remote server can be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, cardio-vibrations (e.g., using accelerometers or microphones), lung vibrations, breath vibrations, sleep related parameters (e.g., snoring, sleep apnea), and tissue fluids, among others.

Figure 19:
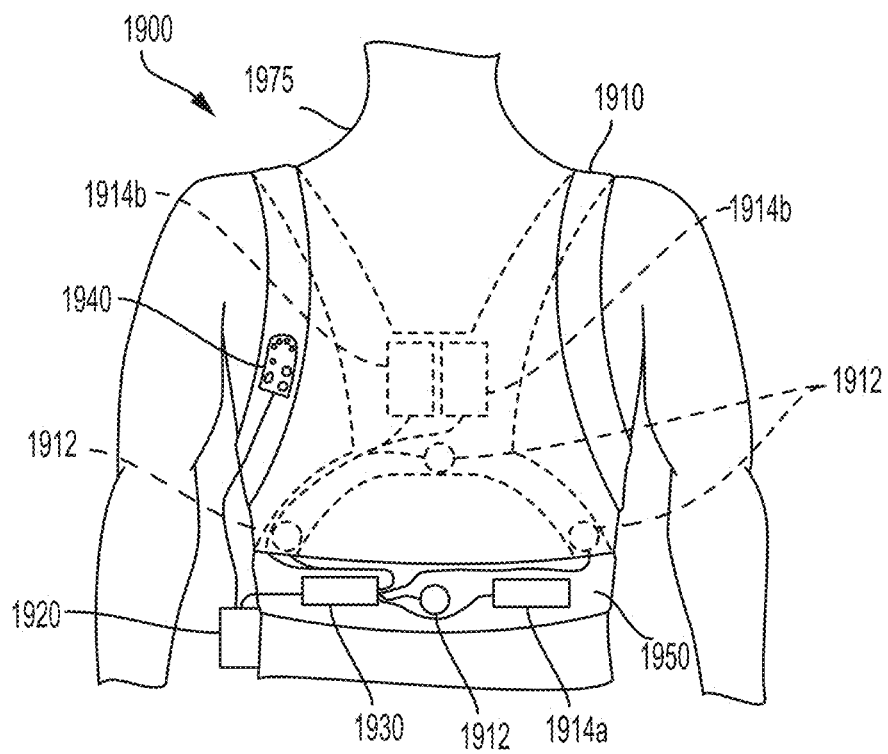
FIG. 19 depicts an embodiment of a patient-worn medical device.

FIG. 19 illustrates an example medical device 1900 that is external, ambulatory, and wearable by a patient 1975, and configured to implement one or more configurations described herein. For example, the medical device 1900 can be a non-invasive medical device configured to be located substantially external to the patient 1975. Such a medical device 1900 can be, for example, an ambulatory medical device that is capable of and designed for moving with the patient as the patient goes about his or her daily routine. For example, the medical device 1900 as described herein can be bodily-attached to the patient via an adhesive pad or via a garment worn about the torso of the patient. For example, the medical device 1900 can be a wearable cardioverter defibrillator. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient, and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1900 can include one or more of the following: a garment 1910, one or more physiological sensors 1912 (e.g., ECG electrodes, heart rate sensors, vibrational sensors, and/or other physiological sensors), one or more therapy electrodes 1914a and 1914b (collectively referred to herein as therapy electrodes 1914), a medical device controller 1920, a connection pod 1930, a patient interface pod 1940, a belt 1950 about the patient's torso to support one or more components, or any combination of these. In some examples, at least some of the components of the medical device 1900 can be configured to be affixed to the garment 1910 (or in some examples, permanently integrated into the garment 1910), which can be worn about the patient's torso.

The medical device controller 1920 can be operatively coupled to the physiological sensors 1912 (e.g., ECG sensors 114 in descriptive examples of the device 100), which can be affixed to the garment 1910, e.g., assembled into the garment 1910 or removably attached to the garment 1910, e.g., using hook and loop fasteners. In some implementations, the physiological sensors 1912 can be permanently integrated into the garment 1910. The medical device controller 1920 can be operatively coupled to the therapy electrodes 1914. For example, the therapy electrodes 1914 can also be assembled into the garment 1910, or, in some implementations, the therapy electrodes 1914 can be permanently integrated into the garment 1910.

Component configurations other than those shown in FIG. 19 are possible. For example, the physiological sensors 1912 can be ECG sensors (e.g., ECG sensors 114) configured to be attached at various positions about the body of the patient 1975. The physiological sensors 1912 can be operatively coupled to the medical device controller 1920 through the connection pod 1930. In some implementations, the physiological sensors 1912 can be adhesively attached to the patient 1975. In some implementations, where the physiological sensors 1912 are ECG electrodes, the ECG electrodes and at least one of the therapy electrodes 1914 can be included on a single integrated patch and adhesively applied to the patient's body.

The physiological sensors 1912 can be configured to detect one or more cardiac signals. Examples of such signals include ECG signals and/or other sensed cardiac physiological signals from the patient 1975. In certain implementations, the physiological sensors 1912 can include additional components such as accelerometers, vibrational sensors (e.g., vibrational sensors 110 of FIG. 1), and other measuring devices for recording additional parameters. For example, the physiological sensors 1912 can also be configured to detect other types of patient physiological parameters and vibrational signals, such as tissue fluid levels, cardio-vibrations, pulmonary-vibrations, respiration-related vibrations of anatomical features in the airway path, patient movement, etc. Example physiological sensors 1912 can include ECG sensors including a metal electrode with an oxide coating such as tantalum pentoxide electrodes, as described in, for example, U.S. Pat. No. 6,253,099 entitled "Cardiac Monitoring Electrode Apparatus and Method," the content of which is incorporate herein by reference.

In examples, the physiological sensors 1912 can include a heart rate sensor for detecting heart beats and monitoring the heart rate of the patient. For instance, such heart rate sensors can include the ECG sensors and associated circuitry described above. In some examples, the heart rate sensors can include a radio frequency based pulse detection sensor or a pulse oximetry sensor worn adjacent an artery of the patient. In implementations, the heart rate sensor can be worn about the wrist of a patient, for example, incorporated on and/or within a watch or a bracelet. In some examples, the heart rate sensor can be integrated within a patch adhesively coupled to the skin of the patient over an artery.

In some examples, the therapy electrodes 1914 can also be configured to include sensors configured to detect ECG signals as well as other physiological signals of the patient 1975. The connection pod 1930 can, in some examples, include ECG circuitry (e.g., ECG circuitry 116 of FIG. 1). For example, such ECG circuitry is configured to amplify, filter, and digitize these cardiac signals. One or more of the therapy electrodes 1914 can be configured to deliver one or more therapeutic defibrillating shocks to the body of the patient 1975 when the medical device 1900 determines that such treatment is warranted based on the signals detected by the sensing electrodes 1912 and processed by the medical device controller 1920. Example therapy electrodes 1914 can include conductive metal electrodes such as stainless steel electrodes that include, in certain implementations, one or more conductive gel deployment devices configured to deliver conductive gel to the metal electrode prior to delivery of a therapeutic shock.

Figure 20:
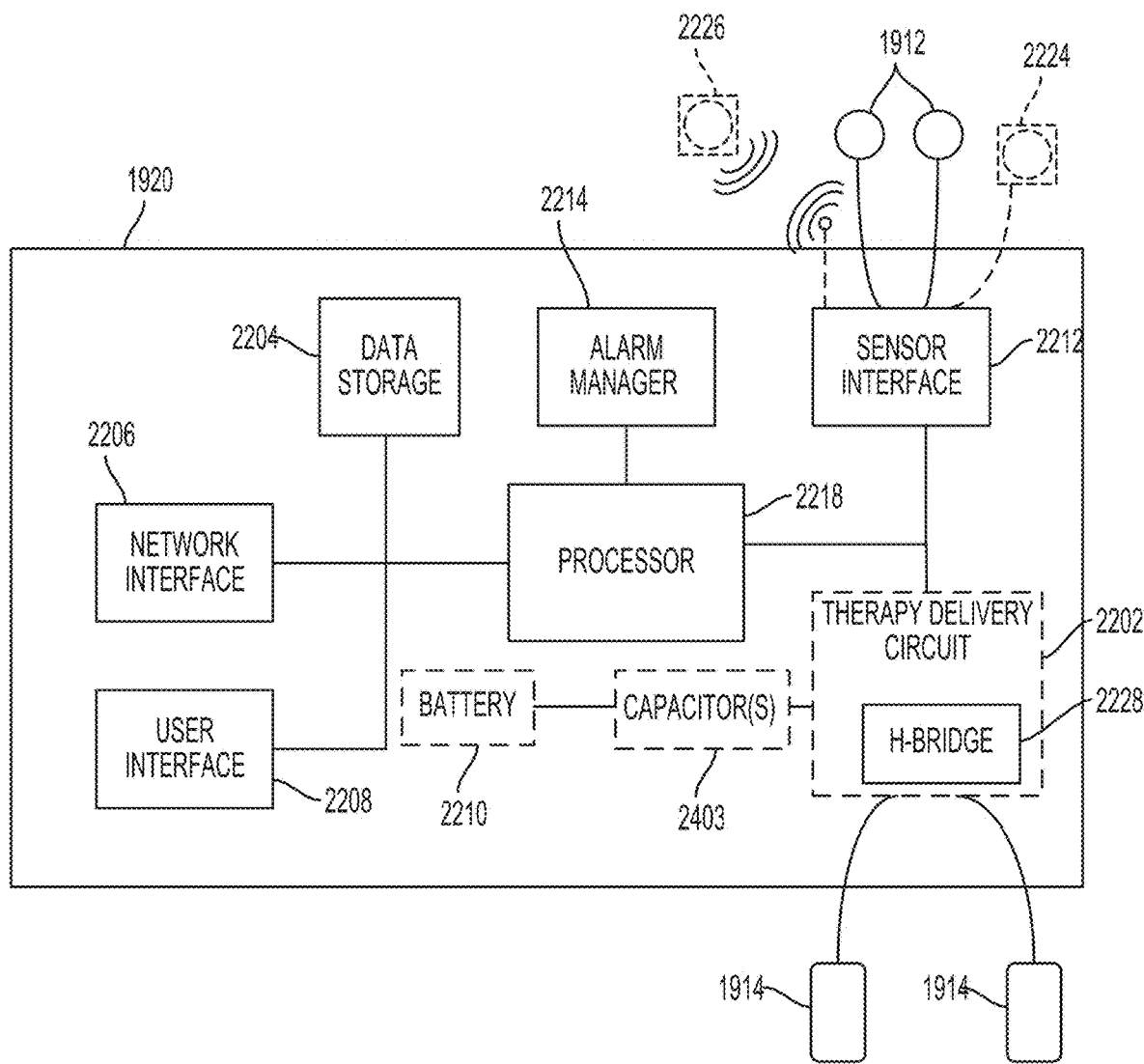
FIG. 20 depicts an embodiment of a medical device controller.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1914 and associated circuitry can be optionally decoupled from (or coupled to) or switched out of (or switched in to) the medical device and this optional mode selection is represented in FIG. 20 by broken lines around selectively employed components. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device. FIG. 20 illustrates a sample component-level view of the medical device controller 1920 for use with implementations of medical devices of the present disclosure. As shown in FIG. 20, the medical device controller 1920 can include a therapy delivery circuit 2202 including a polarity switching component such as an H-bridge 2228, a data storage 2204 (e.g., data storage 105 of FIG. 1), a network interface 2206 (e.g. network interface 106 of FIG. 1), a user interface 2208 (e.g., user interface 108 of FIG. 1), at least one battery 2210, a sensor interface 2212 (e.g., sensor interface 112 of FIG. 1), an alarm manager 2214, least one processor 2218 (e.g., processor 104 of FIG. 1), one or more capacitors 2403, and a battery 2210. A patient monitoring medical device can include a medical device controller 1920 that includes like components as those described with regard to FIG. 20, but does not include the therapy delivery circuit 2202.

The therapy delivery circuit 2202 is coupled to two or more therapy electrodes configured to provide therapy to the patient (e.g., the therapy electrodes 1914 as described above in connection with FIG. 19). For example, the therapy delivery circuit 2202 includes, or is operably connected to, circuitry components that are configured to generate and provide the therapeutic shock. The circuitry components include, for example, resistors, one or more capacitors, relays and/or switches, an electrical bridge such as an H-bridge 2228 (e.g., an H-bridge including a plurality of insulated gate bipolar transistors or IGBTs that deliver and truncate a therapy pulse), voltage and/or current measuring components, and other similar circuitry arranged and connected such that the circuitry work in concert with the therapy delivery circuit and under control of one or more processors (e.g., processor 2218) to provide, for example, one or more pacing or defibrillation therapeutic pulses.

Pacing pulses can be used to treat cardiac arrhythmias such as bradycardia (e.g., in some implementations, less than 30 beats per minute) and tachycardia (e.g., in some implementations, more than 150 beats per minute) using, for example, fixed rate pacing, demand pacing, anti-tachycardia pacing, and the like. Defibrillation pulses can be used to treat ventricular tachycardia and/or ventricular fibrillation.

In implementations, each of the therapy electrodes 1914 has a conductive surface adapted for placement adjacent the patient's skin and has an impedance reducing means contained therein or thereon for reducing the impedance between a therapy electrode and the patient's skin. In implementations, the patient-worn arrhythmia monitoring and treatment device 1900 may include gel deployment circuitry configured to cause the delivery of conductive gel substantially proximate to a treatment site (e.g., a surface of the patient's skin in contact with the therapy electrode 1914) prior to delivering therapeutic shocks to the treatment site. As described in U.S. Pat. No. 9,008,801, titled "WEARABLE THERAPEUTIC DEVICE," issued on Apr. 14, 2015 (hereinafter the "'801 Patent"), which is hereby incorporated herein by reference in its entirety, the gel deployment circuitry can be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry can be coupled to or integrated within a therapy electrode 1914 or other therapy delivery device as a single unit.

When a treatable cardiac condition is detected and no patient response is received after device prompting, the gel deployment circuitry can be signaled to deploy the conductive gel. In some examples, the gel deployment circuitry can be constructed as one or more separate and independent gel deployment modules. Such modules can be configured to receive removable and/or replaceable gel cartridges (e.g., cartridges that contain one or more conductive gel reservoirs). As such, the gel deployment circuitry can be permanently disposed in the garment as part of the therapy delivery systems, while the cartridges can be removable and/or replaceable.

In some implementations, the gel deployment modules can be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry, can be removable and/or replaceable. In some examples, the gel deployment pack, including the one or more gel reservoirs and associated gel deployment circuitry, and the therapy electrode can be integrated into a therapy electrode assembly that can be removed and replaced as a single unit either after use, or if damaged or broken.

Continuing with the description of the example medical device controller 1920 of FIG. 20, in implementations, the one or more capacitors 2403 is a plurality of capacitors (e.g., two, three, four or more capacitors) comprising a capacitor bank. These capacitors 2403 can be switched into a series connection during discharge for a defibrillation pulse. For example, four capacitors of approximately 650 μF can be used. In one implementation, the capacitors can have between 200 to 2500 volt surge rating and can be charged in approximately 5 to 30 seconds from a battery 2210 depending on the amount of energy to be delivered to the patient. Additional implementations of capacitor properties and arrangements on a patient-worn medical device 1900 are provided herein in subsequent sections.

For example, each defibrillation pulse can deliver between 60 to 400 joules (J) of energy. In some implementations, the defibrillating pulse can be a biphasic truncated exponential waveform, whereby the signal can switch between a positive and a negative portion (e.g., charge directions). An amplitude and a width of the two phases of the energy waveform can be automatically adjusted to deliver a predetermined energy amount.

The data storage 2204 (e.g. data storage 105 of FIG. 1) can include one or more of non-transitory computer readable media, such as flash memory, solid state memory, magnetic memory, optical memory, cache memory, combinations thereof, and others. The data storage 2204 can be configured to store executable instructions and data used for operation of the medical device controller 1920. In certain implementations, the data storage 2204 can include executable instructions that, when executed, are configured to cause the processor 2218 to perform one or more functions.

In some examples, the network interface 2206 can facilitate the communication of information between the medical device controller 1920 and one or more other devices or entities over a communications network. For example, where the medical device controller 1920 is included in an ambulatory medical device (such as medical device 1900), the network interface 2206 can be configured to communicate with a remote computing device such as a remote server or other similar computing device. The network interface 2206 can include communications circuitry for transmitting data in accordance with a Bluetooth® wireless standard for exchanging such data over short distances to an intermediary device(s) (e.g., a base station, a "hotspot" device, a smartphone, a tablet, a portable computing device, and/or other devices in proximity of the wearable medical device 100). The intermediary device(s) may in turn communicate the data to a remote server over a broadband cellular network communications link, The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain implementations, the user interface 2208 can include one or more physical interface devices such as input devices, output devices, and combination input/output devices and a software stack configured to drive operation of the devices. These user interface elements may render visual, audio, and/or tactile content. Thus, the user interface 2208 may receive input or provide output, thereby enabling a user to interact with the medical device controller 1920. In some implementations, the user interface 2208 can be implanted as a hand-held user interface device. (See, for example, the patient interface pod 1940 of FIG. 19.) For instance, the hand-held user interface device can be a smartphone or other portable device configured to communicate with the controller 1920 via the network interface 2206. In an implementation, the hand-held user interface device may also be the intermediary device for facilitating the transfer of information from the device 1900 to the remote server.

As described, the medical device controller 1920 can also include at least one battery 2210 configured to provide power to one or more components, such as the one or more capacitors 2403, integrated in the medical device controller 1920 or, in some embodiments, into the garment 1910 of the medical device 1900. The battery 2210 can include a rechargeable multi-cell battery pack. In one example implementation, the battery 2210 can include three or more 2200 mAh lithium ion cells that provide electrical power to the other device components within the medical device controller 1920. For example, the battery 2210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 1920.

The sensor interface 2212 can be coupled to one or more sensors configured to monitor one or more physiological parameters of the patient. As shown in FIG. 2, the sensors can be coupled to the medical device controller 1920 via a wired or wireless connection. The sensors can include one or sensing electrodes 1912 (e.g., electrocardiogram (ECG) electrodes 1912 and ECG sensors 114 of FIG. 1), vibrations sensors 2224 (e.g. vibrational sensors 110), and tissue fluid monitors 2226 (e.g., based on ultra-wide band radiofrequency devices). For example, the sensor interface 2212 can include ECG circuitry (such as ECG circuitry 116 of FIG. 1) and/or accelerometer circuitry (e.g., accelerometer circuitry 120 of FIG. 1), which are each configured to receive and condition the respective sensor signals.

The sensing electrodes 1912 can monitor, for example, a patient's ECG information. For example, the sensing electrodes 1912 of FIG. 20 and ECG sensing electrodes 114 of FIG. 1, can include conductive electrodes with stored gel deployment (e.g., metallic electrodes with stored conductive gel configured to be dispersed in the electrode-skin interface when needed), or dry electrodes (e.g., a metallic substrate with an oxide layer in direct contact with the patient's skin). The sensing electrodes 1912, 114 can be configured to measure the patient's ECG signals. The sensing electrodes 1912, 114 can transmit information descriptive of the ECG signals to the sensor interface 2212, 112 for subsequent analysis.

The vibrational sensors 2224 can detect a patient's cardiac or pulmonary (cardiopulmonary) vibration information. For example, the cardiopulmonary vibrations sensors 2224 can be configured to detect cardio-vibrational biomarkers in a cardio-vibrational signal, including any one or all of S1, S2, S3, and S4 cardio-vibrational biomarkers. From these cardio-vibrational biomarkers, certain electromechanical metrics can be calculated, including any one or more of electromechanical activation time (EMAT), percentage of EMAT (% EMAT), systolic dysfunction index (SDI), left ventricular diastolic perfusion time (LDPT), and left ventricular systolic time (LVST). The cardiopulmonary vibrations sensors 2224 may also be configured to detect heart wall motion, for example, by placement of the sensor 2224 in the region of the apical beat.

The vibrations sensors 2224, 110 can include an acoustic sensor configured to detect vibrations from a subject's cardiac or pulmonary (cardiopulmonary) system and provide an output signal responsive to the detected vibrations of the targeted organ. For instance, in some implementations, the vibrations sensors 2224 are able to detect vibrations generated in the trachea or lungs due to the flow of air during breathing. The vibrations sensors 2224, 110 can also include a multi-channel accelerometer, for example, a three channel accelerometer configured to sense movement in each of three orthogonal axes such that patient movement/body position can be detected. The vibrations sensors 2224, 110 can transmit information descriptive of the cardiopulmonary vibrations information or patient position/movement to the sensor interface 2212, 112 for subsequent analysis.

The tissue fluid monitors 2226 can use radio frequency (RF) based techniques to assess changes of accumulated fluid levels over time. For example, the tissue fluid monitors 2226 can be configured to measure fluid content in the lungs (e.g., time-varying changes and absolute levels), for diagnosis and follow-up of pulmonary edema or lung congestion in heart failure patients. The tissue fluid monitors 2226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 2226 can transmit information descriptive of the tissue fluid levels to the sensor interface 2212 for subsequent analysis.

The sensor interface 2212 can be coupled to any one or combination of sensing electrodes/other sensors to receive other patient data indicative of patient parameters. Once data from the sensors has been received by the sensor interface 2212, the data can be directed by the processor 2218 to an appropriate component within the medical device controller 1920. For example, if cardiac data is collected by the cardiopulmonary vibrations sensor 2224 and transmitted to the sensor interface 2212, the sensor interface 2212 can transmit the data to the processor 2218 which, in turn, relays the data to a cardiac event detector. The cardiac event data can also be stored on the data storage 2204.

An alarm manager 2214 can be configured to manage alarm profiles and notify one or more intended recipients of events specified within the alarm profiles as being of interest to the intended recipients. These intended recipients can include external entities such as users (e.g., patients, physicians, other caregivers, patient care representatives, and other authorized monitoring personnel) as well as computer systems (e.g., monitoring systems or emergency response systems). The alarm manager 2214 can be implemented using hardware or a combination of hardware and software.

For instance, in some examples, the alarm manager 2214 can be implemented as a software component that is stored within the data storage 2204 and executed by the processor 2218. In this example, the instructions included in the alarm manager 2214 can cause the processor 2218 to configure alarm profiles and notify intended recipients according to the configured alarm profiles. In some examples, alarm manager 2214 can be an application-specific integrated circuit (ASIC) that is coupled to the processor 2218 and configured to manage alarm profiles and notify intended recipients using alarms specified within the alarm profiles. Thus, examples of alarm manager 2214 are not limited to a particular hardware or software implementation.

In some implementations, the processor 2218 (e.g., processor 104 of FIG. 1) includes one or more processors (or one or more processor cores) that each are configured to perform a series of instructions that result in manipulated data and/or control the operation of the other components of the medical device controller 1920. In some implementations, when executing a specific process (e.g., cardiac monitoring), the processor 2218 can be configured to make specific logic-based determinations based on input data received, and be further configured to provide one or more outputs that can be used to control or otherwise inform subsequent processing to be carried out by the processor 2218 and/or other processors or circuitry with which processor 2218 is communicatively coupled. Thus, the processor 2218 reacts to a specific input stimulus in a specific way and generates a corresponding output based on that input stimulus. In some example cases, the processor 2218 can proceed through a sequence of logical transitions in which various internal register states and/or other bit cell states internal or external to the processor 2218 can be set to logic high or logic low. The processor 2218 can be configured to execute a function stored in software. For example, such software can be stored in a data store coupled to the processor 2218 and configured to cause the processor 2218 to proceed through a sequence of various logic decisions that result in the function being executed. The various components that are described herein as being executable by the processor 2218 (e.g., processor 104 of FIG. 1) can be implemented in various forms of specialized hardware, software, or a combination thereof. For example, the processor can be a digital signal processor (DSP) such as a 24-bit DSP processor. The processor can be a multi-core processor, e.g., a processor having two or more processing cores. The processor can be an Advanced RISC Machine (ARM) processor such as a 32-bit ARM processor or a 64-bit ARM processor. The processor can execute an embedded operating system and include services provided by the operating system that can be used for file system manipulation, display & audio generation, basic networking, firewalling, data encryption and communications.

In implementations, the therapy delivery circuit 2202 includes, or is operably connected to, circuitry components that are configured to generate and provide the therapeutic shock. As described previously, the circuitry components include, for example, resistors, one or more capacitors 2403, relays and/or switches, an electrical bridge such as an H-bridge 2228 (e.g., an H-bridge circuit including a plurality of switches, (e.g. insulated gate bipolar transistors or IGBTs, silicon carbide field effect transistors (SiC FETs), metal-oxide semiconductor field effect transistors (MOSFETS), silicon-controlled rectifiers (SCRs), or other high current switching devices)), voltage and/or current measuring components, and other similar circuitry components arranged and connected such that the circuitry components work in concert with the therapy delivery circuit 2202 and under control of one or more processors (e.g., processor 2218) to provide, for example, one or more pacing or defibrillation therapeutic pulses.

In implementations, the device 1900 further includes a source of electrical energy, for example, the one or more capacitors 2403, that stores and provides energy to the therapy delivery circuit 2202. The one or more therapeutic pulses are defibrillation pulses of electrical energy, and the one or more treatable arrhythmias include ventricular fibrillation and ventricular tachycardia. In implementations, the one or more therapeutic pulses are biphasic exponential pulses. Such therapeutic pulses can be generated by charging the one or more capacitors 2403 and discharging the energy stored in the one or more capacitors 2403 into the patient. For example, the therapy delivery circuit 2202 can include one or more power converters for controlling the charging and discharging of the one or more capacitors 2403. In some implementations, the discharge of energy from the one or more capacitors 2403 can be controlled by, for example, an H-bridge that controls the discharge of energy into the body of the patient 1975, like the H-bridge circuit described in U.S. Pat. No. 6,280,461, titled "PATIENT-WORN ENERGY DELIVERY APPARATUS," issued on Aug. 28, 2001, and U.S. Pat. No. 8,909,335, titled "METHOD AND APPARATUS FOR APPLYING A RECTILINEAR BIPHASIC POWER WAVEFORM TO A LOAD," issued on Dec. 9, 2014, each of which is hereby incorporated herein by reference in its entirety.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A patient-worn ambulatory cardiac monitoring device for monitoring a patient during a patient activity, comprising:
   at least one physiological sensor configured to detect signals indicative of cardiac activity, the at least one physiological sensor comprising an ECG sensor configured to monitor an ECG signal of the patient;
   an activity sensor and associated circuitry configured to monitor patient movements;
   a vibrational sensor configured to monitor a cardio-vibrational signal of the patient; and
   at least one processor in communication with the at least one physiological sensor, the activity sensor, and the vibrational sensor, and configured to
      request that the patient initiate a first patient activity during a baseline period;

determine that the patient has been engaged in the first patient activity of the baseline period for a predetermined amount of time based on the patient's heart rate;

record one or more baseline electromechanical time intervals during the first patient activity of the baseline period;

store the one or more baseline electromechanical time intervals in a memory;

after the baseline period, determine initiation of a second patient activity;

determine that the patient has been engaged in the second patient activity for the predetermined amount of time based on the patient's heart rate;

during the second patient activity and after determining that the patient has been engaged in the second patient activity for the predetermined amount of time, measure a plurality of electromechanical time intervals between an ECG fiducial point in the ECG signal and a cardio-vibrational fiducial point in the cardio-vibrational signal during at least one cardiac cycle of the patient's heart;

determine a representative electromechanical time interval value for the plurality of electromechanical time intervals;

determine a trend relating to the electromechanical time intervals for the patient using at least the one or more baseline electromechanical time intervals recorded during the first patient activity of the baseline period and the representative electromechanical time interval value for the plurality of electromechanical time intervals measured during the second patient activity; and issue an alert indicating a continued or worsening heart failure condition based on the determined trend relating to the electromechanical time intervals.

2. The device of claim 1, wherein the at least one processor is configured to retrieve the one or more baseline electromechanical time intervals from the memory, compare the representative electromechanical time interval with the one or more baseline electromechanical time intervals, provide an output based on the comparison, and identify an improving or worsening heart failure condition of the patient based on the output.

3. The device of claim 2, wherein the at least one processor is configured to provide the output based on the comparison when the representative electromechanical time interval falls outside of a range of within at least one of: 1% of the one or more baseline electromechanical time intervals, 2% of the one or more baseline electromechanical time intervals, 5% of the one or more baseline electromechanical time intervals, 10% of the one or more baseline electromechanical time intervals, 15% of the one or more baseline electromechanical time intervals, or 20% of the one or more baseline electromechanical time intervals.

4. The device of claim 1, wherein the at least one processor is configured to retrieve at least one of a standard electromechanical time interval or a standard electromechanical time interval range, compare the representative electromechanical time interval with the retrieved at least one of the standard electromechanical time interval or the standard electromechanical time interval range, and provide an output based on the comparison.

5. The device of claim 4, wherein the standard electromechanical time interval comprises a value selected from a range of 80 ms to 150 ms, and wherein the standard electromechanical time interval range comprises the range of 80 ms to 150 ms.

6. The device of claim 4, wherein the at least one processor is configured to provide the output based on the comparison when the representative electromechanical time interval falls outside of a range of within at least one of: 1% of the standard electromechanical time interval, 2% of the standard electromechanical time interval, 5% of the standard electromechanical time interval, 10% of the standard electromechanical time interval, 15% of the standard electromechanical time interval, or 20% of the standard electromechanical time interval, and wherein the at least one processor is configured to identify an improving or worsening heart failure condition of the patient based on the output.

7. The device of claim 1, wherein the at least one processor is further configured to measure, during the patient activity, a cardio-vibrational time interval from a first cardio-vibrational fiducial point of an S1 cardio-vibrational biomarker to a second cardio-vibrational fiducial point of an S2 cardio-vibrational biomarker for the cardiac cycle.

8. The device of claim 7, wherein the cardio-vibrational time interval comprises a left ventricular systolic time (LVST) interval.

9. The device of claim 1, wherein the at least one processor is further configured to measure, during the patient activity, an S3 cardio-vibrational biomarker strength derived from the cardio-vibrational signal.

10. The device of claim 1, wherein the device comprises a wearable defibrillator comprising a garment configured to be worn about a torso of the patient, and at least two therapy electrodes supported by the garment and configured to deliver energy to the torso of the patient, wherein the at least one physiological sensor is supported by the garment.

11. The device of claim 1, wherein the patient activity has an activity duration of between at least 3 to 6 minutes, between at least 6 to 12 minutes, between at least 12 to 15 minutes, between at least 15 to 20 minutes, between at least 20 to 30 minutes, between at least 30 to 45 minutes, or between at least 45 minutes to an hour.

12. The device of claim 1, wherein the at least one electromechanical time interval begins from the ECG fiducial point comprising at least one of a point on a P-wave segment of the ECG signal, a point on a P-Q segment of the ECG signal, a point on a Q-wave segment of the ECG signal, a point on an R-wave segment of the ECG signal, or a point at the beginning of the R-wave segment, and ends at the cardio-vibrational fiducial point, wherein the cardio-vibrational fiducial point occurs within an S1 cardio-vibrational biomarker of the cardio-vibrational signal.

13. The device of claim 1, wherein the at least one processor is configured to measure an RR interval of the ECG signal and calculate a ratio of the at least one electromechanical time interval to the RR interval.

14. The device of claim 1, wherein the at least one electromechanical time interval begins from the cardio-vibrational fiducial point within an S2 cardio-vibrational biomarker of the cardio-vibrational signal and ends at the ECG fiducial point at an onset of a next Q wave in the ECG signal.

15. The device of claim 14, wherein the at least one electromechanical time interval comprises a left ventricular diastolic perfusion time (LDPT) interval.

16. The device of claim 1, wherein the at least one electromechanical time interval comprises an electromechanical activation time (EMAT) interval.

17. The device of claim 16, wherein the at least one processor is configured to calculate a ratio of at least one of an: EMAT interval/LVST interval, EMAT interval/LDPT interval, or EMAT interval/RR interval.

18. The device of claim 1, wherein the device further comprises a heart rate sensor, and wherein the determination that the patient has been engaged in the first patient activity of the baseline period for the predetermined amount of time based on the patient's heart rate is based on heart rate information from the heart rate sensor.

19. The device of claim 18, wherein the heart rate sensor comprises the ECG sensor, and wherein the heart rate information of the patient is calculated from the ECG signal of the ECG sensor.

20. The device of claim 1, wherein determining the trend relating to the electromechanical time interval for the patient comprises determining a trend line for the patient using at least the one or more baseline electromechanical time intervals recorded during the first patient activity of the baseline period and the at least one electromechanical time interval measured during the second patient activity.

21. The device of claim 1, wherein the representative electromechanical time interval value comprises an average of the plurality of electromechanical time intervals, a median of the plurality of electromechanical time intervals, a mode of the plurality of electromechanical time intervals, or a random electromechanical time interval from the plurality of electromechanical time intervals.

\* \* \* \* \*